US006352825B1

(12) United States Patent
Meijer et al.

(10) Patent No.: US 6,352,825 B1
(45) Date of Patent: *Mar. 5, 2002

(54) HUMAN PAPILLOMA VIRUS DETECTION IN A NUCLEIC ACID AMPLIFICATION PROCESS USING GENERAL PRIMERS

(75) Inventors: Christophorus Joannes Meijer, Leiden; Adrianus Johannes van den Brule, 's-Hertogenbosch; Jan Marcus Walboomers, Amsterdam; Petrus Josephus Snijders, Amstelveen, all of (NL)

(73) Assignee: Stichting Researchfonds Pathologie, Amsterdam (NL)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/696,932
(22) PCT Filed: Feb. 20, 1995
(86) PCT No.: PCT/NL95/00066
    § 371 Date: Nov. 25, 1996
    § 102(e) Date: Nov. 25, 1996
(87) PCT Pub. No.: WO95/22626
    PCT Pub. Date: Aug. 24, 1995

(30) Foreign Application Priority Data

Feb. 21, 1994 (EP) ............................................. 94200432
Sep. 23, 1994 (EP) ............................................. 94202739

(51) Int. Cl.[7] .......................... C12Q 1/68; C12P 19/34; C07H 21/04
(52) U.S. Cl. .............................. 435/5; 435/6; 435/91.2; 435/91.52; 536/23.72; 536/24.32; 536/24.33
(58) Field of Search ............................... 435/5, 6, 91.2, 435/91.52; 536/23.72, 24.32, 24.33; 935/8, 17, 78

(56) References Cited

U.S. PATENT DOCUMENTS 5,527,898 A * 6/1996 Bauer ......................... 536/24.3

FOREIGN PATENT DOCUMENTS

| EP | 0477972 | * | 4/1992 |
| WO | 8905357 | * | 6/1989 |
| WO | 910675 | * | 7/1991 |

OTHER PUBLICATIONS

Compton, Nature (1991) 350: 91–92.*
Van der Brule et al, Journal of Clinical Chemistry (1992) 30:1716–1721.*
Pollard–Knight Technique (1990) 2:113–132.*
Shionogi, Derwent Abstract AN 92-111672, Feb. 1992 (JP-A-0458888).*

* cited by examiner

Primary Examiner—Carla J. Myers
(74) Attorney, Agent, or Firm—Robert D. Katz; Cooper & Dunham, LLP

(57) ABSTRACT

The oligonucleotides: (i) the 23-mer 5'-TTTGTTACTGTGGTAGATACTAC-3' (SEQ ID NO: 1) or the 23-mer which is complementary to it; (ii) a 23-mer derived from (i) by from 1 to 5 nucleotide substitutions; (iii) a 23[+]-mer having a 3' terminal sequence consisting of (i) or (ii); (iv) a fragment of (i) or (ii) having a length of from 8 to 18 nucleotides; (v) the 25-mer 5'-GAAAAATAAACTGTAAATCATATTC-3' (SEQ ID NO: 2) or the 25-mer which is complementary to it; (vi) a 25-mer derived from (v) by from 1 to 5 nucleotide substitutions; (vii) a 25[+]-mer having a 3' terminal sequence consisting of (v) or (vi); (viii) the 28-mer 5'-GAAAAATAAACTGTAAATCATATTCTTC-3' (SEQ ID NO: 10) or the 28-mer which is complementary to it; (ix) the 28-mer 5'-GAAAAATAAACTGTAAATCATATTCCTC-3' (SEQ ID NO: 18) or the 28-mer which is complementary to it; (x) a 28-mer derived from (viii) or (ix) by from 1 to 5 nucleotide substitutions; (xi) a 28[+]-mer having a 3' terminal sequence consisting of (viii), (ix) or (x); (xii) a fragment of (v), (vi), (vii), (ix) or (x) having a length of from 8 to 18 nucleotides, useful as a primer in a nuc acid amplification process, e.g. a general primer PCR or NASBA, or LCR, to amplify DNA of genital HPV genotypes, e.g. in a method of analyzing a sample for the presence therein of HPV.

24 Claims, No Drawings

HUMAN PAPILLOMA VIRUS DETECTION IN A NUCLEIC ACID AMPLIFICATION PROCESS USING GENERAL PRIMERS

This application is the National Stage of International application No. PCT/NL95/00066, filed Feb. 20, 1995.

FIELD OF THE INVENTION

The invention is in the field of sample analysis to determine the presence therein of Human Papilloma Virus (HPV) genotypes by amplifying HPV DNA present in the sample with a nucleic acid amplification process, e.g. the Polymerase Chain Reaction (PCR), using general primers (GPs). More in particular, the invention relates to an analysis of cervical smears which allows cervical carcinoma-related diagnosis and prognosis wherein the analysis comprises a GP-nucleic acid amplification process, e.g. GP-PCR, to determine whether the sample contains any HPV, followed by a typing of the HPV genotype present.

BACKGROUND OF THE INVENTION

HPV comprises over 70 different epitheliotropic genotypes of which over 30 are mucosotropic. Approximately one third of these mucosotropic HPV genotypes have been isolated from or associated with cervical carcinomas (De Villiers, 1989; zur Hausen, 1991).

The PCR method has been introduced as the most sensitive method for the detection of HPV DNA in clinical specimens. However, a significant heterogeneity at the nucleotide level is found between the different HPV genotypes. This has hampered the development of a simple universal PCR test for the detection of all HPV genotypes. Despite this, HPV-PCR methods have been developed which allow the detection of a broad spectrum of mainly mucosotropic HPV genotypes (Manos et al., 1989; Gregoire et al., 1989; Snijders et al., 1990).

A combination of the general primers GP5 and GP6, originally selected from the HPV L1 region on the basis of sequence information of HPV6, HPV11, HPV16, HPV18, HPV31 and HPV33 (Snijders et al., 1990; WO 91/10675), was found to amplify target DNA of at least 27 mucosotropic HPV genotypes under conditions that allow mismatch acceptance (Van den Brule et al., 1990a, 1992; de Roda Husman et al., 1994a). The strength of this GP5/6-mediated PCR method has been substantiated further by the detection of HPV DNA in 100% of cervical scrapes classified cytomorphologically as Pap IV (carcinoma in situ) and Pap V (carcinoma) in the Netherlands (Van den Brule et al., 1991; de Roda Husman et al., 1994a). This suggests that in the Dutch population all genital high risk HPVs can be detected by this assay.

Still, using GP-PCR in routine diagnostic practice, it has been found that a small number of clinical samples gives rise to ambiguous results, reflected by GP-PCR signals that are weaker than signals obtained from 50–100 Siha cells (which contain one copy of HPV16 per cell; Van den Brule et al., 1990a). This may complicate interpretation of screening results since it is presently unknown whether the weak signals represent a cross-reaction with cellular sequences or the presence of HPV genotypes which show a reduced sensitivity in the GP-PCR. It has been shown previously that some HPV types like HPV30 are detected with a decreased sensitivity in the GP-PCR (Snijders et al., 1990), and also the recently sequenced HPV types HPV39 and HPV51, showing more than three mismatches with one of the primers, have revealed a reduction in GP-PCR sensitivity (data not shown). Furthermore, some HPV types (e.g. HPV18) give rise to additional bands in the GP5/6 PCR (Snijders et al., 1990).

Recently, several groups have found that despite the presence of primer/template mismatches, a successful amplification by PCR can be ensured by the presence of perfectly matching nucleotides at the 3'-ends of the primers (Newton et al., 1989; Sommer and Tautz, 1989; Evander and Wadell, 1991).

Moreover, it also has been found that increased primer length contributes to a more efficient amplification, probably by increasing the stability of the primer/template complex (Mack and Sninsky, 1988).

Sequence analysis of the GP5/6 PCR products of different HPV genotypes has revealed the presence of HPV-specific amino acid consensus sequences directly adjacent to the 3'-ends of GP5 and GP6 (Van den Brule et al., 1992). We investigated the utility of GP5/6 primers elongated with highly conserved sequences at their 3'-ends. These elongated primers (named GP5+ and GP6+) were tested in the PCR using a model system of cloned HPV DNAs and subsequently evaluated on cervical smears which previously showed ambiguous or negative results with the original GP5/6 assay.

The results surprisingly revealed that an elongation of GP5 and GP6 with conserved sequences at their 3'-ends can overcome reduced PCR efficiencies most likely related to the number of primer/target mismatches and increase primer-template stability. Moreover, the use of elongated GP5/6 in the PCR resulted in the clarification of HPV status in cytomorphologically normal cervical scrapes which previously showed ambiguous or negative GP-PCR results.

Another desideratum in the field of HPV detection is a means to differentiate quickly between high risk and low risk HPV types. So far, individual HPV typing has been performed on the products of nucleic acid amplification by hybridization analysis using HPV type-specific oligonucleotide probes or probes consisting of cloned HPV types, or by additional type-specific PCRs. This kind of analysis entails much work, especially if one considers that the clinician usually wants to know only whether there is a high or low risk of cervical cancer. It is known by now that only a restricted group of 15 HPV types (Nos. 16, 18, 31, 33, 35, 39, 45, 51, 52, 54, 56, 58, 59, 66 and 68) is associated with cervical carcinomas and carcinomas in situ (see the review of De Villiers, 1989). In a recent study it was found that 10 different HPV types (Nos. 6, 16, 18, 31, 33, 45, 51, 52, 54 and 58) were present in PAP IV scrapes tested by GP-PCR (De Roda Husman et al., 1994b). Furthermore, preliminary results from follow up studies show that only high risk HPV types show progression from cytologically normal cervix to cervical intraepithelial neoplasia (CIN) III. Classification into HPV groups with different biological behaviour instead of individual HPV typing would be less confusing and will be appreciated by the clinician. HPV detection assays using a panel of high risk HPV probes will detect most HPV-induced carcinomas and carcinomas in situ. So, for the sake of an early detection of cervical cancer, there is a need for HPV detection assays permitting a rapid differentiation between all known high risk and low risk HPV types.

We herein describe the design and performance of type-specific oligonucleotide probes which may be used either separately or in the form of cocktails for screening the GP5+/6+ mediated DNA amplification products on high and low risk HPV genotypes.

SUMMARY OF THE INVENTION

Sequence analysis of HPV GP5/6-mediated PCR products has revealed the presence of short highly conserved sequences adjacent to the 3'-ends of both primers. Since perfect matching of 3' primer ends is critical for an efficient PCR and elongation of primers gives an additional stabilization of primer/template complexes, part of these sequences were used to elongate GP5 and GP6 at their 3'-ends. Using reconstruction experiments with different molecularly cloned HPVs, the elongated primers (named GP5+ and GP6+) showed a clearly improved detection of especially HPV genotypes having more than 3 mismatches with one or both primers. The strength of the method was further substantiated by improved HPV detection in cytomorphologically normal cervical scrapes which showed ambiguous results in the original HPV GP5/6-mediated PCR. Also a small percentage of cytological normal scrapes which were originally HPV-negative with HPV GP5/6-mediated PCR became positive after application of the elongated GP5/6 primers.

Therefore, the invention provides a general primer pair GP5/6 which has been elongated at the 3'-ends with adjacent highly conserved sequences thereby improving HPV detection in cervical smears.

Furthermore, by computer-assisted sequence analyses of the amplication product obtained by GP5/6 and GP5+/6+ PCR, which amplification product has a length of about 150 bp, we selected (from the internal part of the GP5/6 region) 30-mer oligonucleotides specific for 24 different HPV genotypes. These new oligonucleotides, suitably labeled with e.g. digoxygenine, proved useful as HPV-specific probes in Southern blot analysis of high copy PCR products derived from the same HPV types. No cross-hybridisations were found. We made two cocktails which enabled a specific and sensitive differentiation between HPV types of high risk (Nos. 16, 18, 31, 33, 35, 39, 45, 51, 52, 54, 56 and 58) and low risk (Nos. 6, 11, 34, 40, 42, 43 and 44) for the development of cervical cancer. These probe cocktails may be succesfully applied for a rapid identification of high risk HPV types in GP-PCR based HPV screening of cervical scrapes.

DETAILED DESCRIPTION OF THE INVENTION

The invention provides an oligonucleotide selected from the group consisting of
(i) the 23-mer 5'-TTTGTTACTGTGGTAGATACTAC-3' (SEQ ID NO:1) or the 23-mer which is complementary to SEQ ID NO:1;
(ii) a 23-mer derived from (i) by from 1 to 5 nucleotide substitutions;
(iii) a 23⁺-mer having a 3' terminal sequence consisting of (i) or (ii);
(iv) a fragment of (i) or (ii) having a length of from 8 to 18 nucleotides.

The oligonucleotide (i) is derived from a relatively conserved part of the L1 region of HPV. The 23-mer of SEQ ID NO:1 is composed of the primer GP5, as described in WO91/10675, and an extension at the 3' terminus of the three additional nucleotides TAC. In view of said 3' extension, it is referred to herein as GP5+.

The invention also includes the complementary sequence, which may be useful in certain kinds of nucleic acid amplification methods, such as in the LCR (Ligase Chain Reaction; see Barany 1991). In view of the possibility to use LCR technology, the invention also includes fragments of (i) which contain from 8 to 18 nucleotides. Preferably, said fragments correspond to either the 5'-end or the 3'-end of (i). The invention also includes such fragments of from 8 to 18 nucleotides of (ii), (v), (vi), (viii), (ix) and (x), which will be described furtheron.

In the LCR, a thermostable ligase is used for a cyclic joining of two oligonucleotides that are substantially adjacent to each other. "Substantially adjacent" means that the distance between the two oligonucleotides is sufficiently small to allow the ligase enzyme to ligate the two oligonucleotides. Preferably, the two oligonucleotides are immediately adjacent to each other. LCR cycli consist of denaturation, annealing and ligation steps similar to the PCR. Thus, a newly formed oligonucleotide after ligation serves as a target for the annealing and ligation of the complementary oligonucleotides and, consequently, an exponential enrichment can be achieved.

With respect to HPV detection, LCR technology may be used. By using as primers in said LCR, one of the general primers of this invention, together with an oligonucleotide complementary thereto, plus a primer based on an adjacent sequence, together with an oligonucleotide complementary thereto, it is possible, depending on the choice of these latter primer sequences, to make amplification dependent on the presence of particular HPV types or groups of HPV types.

Alternatively, LCR may be carried out using a pair of general primers of this invention plus oligonucleotides complementary thereto, wherein the pair of general primers of this invention consists of two different fragments of the same general primer. Preferably, one fragment corresponds to the 5'-end of said general primer and the other fragment corresponds to the 3'-end of said general primer, and the two fragments do not overlap but are substantially adjacent sequences. The fragments should have a length of from 8 to 18 nucleotides. An LCR based on the use of such fragments of the same general primer is useful for the detection of genital HPV genotypes in general.

The oligonucleotide (ii) is derived from SEQ ID NO:1, or from its complementary sequence, by from 1 to 5 nucleotide substitutions. Preferably, said substitutions concern substitutions occurring between different HPV strains. For example, the 4th nucleotide (G) is substituted in some strains by C (in HPV32, HPV39 and HPV57), in others by T (in HPV42), in others by A (in HPV51). Therefore, the invention covers oligonucleotides which contain any one of these, or similar substitutions.

Preferably, however, nucleotide substitutions which give rise to self-annealing or hair-pin loop formation of the oligonucleotide molecules are avoided. For example, substitution of the 21st nucleotide (T) by C is less preferred as the resulting molecule is prone to self-annealing or hair-pin loop formation, for example as follows:

The oligonucleotide (iii) is a 23+-mer, i.e. an oligonucleotide of more than 23 nucleotides. The 3' terminal sequence consists of oligonucleotide (i) or oligonucleotide (ii). The extension at the 5'-end may have any length. Preferably, however, the total length of the oligonucleotide is not more than 50 nucleotides, more preferably not more than 40 nucleotides. Shorter oligonucleotides, such as those consisting of exactly 23 nucleotides, can be prepared more readily in good yield, whereas longer oligonucleotides may be preferable in view of higher efficiency in the PCR, or because the added sequence at the 5'-end brings a practical advantage.

For example, the added sequence at the 5'-end may comprise one or more restriction enzyme recognition sequences (restriction sites) such as, for example, BamHI, EcoRI and HindIII sites. Such primers are identified herein as Res primers. In addition to the advantage of a higher efficiency in the PCR, these extended oligonucleotides have the practical advantage of facilitating direct cloning of the amplimers obtained in the PCR, for instance into the plasmid pBR322 and into plasmids derived therefrom, such as p.Gemini vectors. Thus, the amplimers can be made suitable for conventional double-stranded sequencing (cloning capacity of 100 bp to several kb). The amplimers can also be cloned into the phage M13 (mp 18 and 19) for single-stranded sequencing (cloning capacity 100–500 bp). Owing to rapid developments in the field of sequencing techniques, direct sequencing of the amplimers is also one of the options. Direct sequencing of the amplimer products even seems to be the best identification for the virus. See WO91/10675 which, in its entirety, is incorporated herein by reference.

As another example, the added sequence at the 5'-end may comprise a promoter sequence such as, for example, a T7 promoter sequence which is:

5'-AAT TCT AAT ACG ACT CAC TAT AGG GGG A -3'  (SEQ ID NO:26);

or a T3 promoter sequence which is:

5'-TTA TTA ACC CTC ACT AAA GGG AAG -3'(SEQ ID NO:27);

or a SP6 promoter sequence which is:

5'-ATT TAG GTG ACA CTA TAG AAT AC-3'  (SEQ ID NO:28).

Such primers, which may include an insertion of one or more nucleotides between the promoter sequence and the 3' terminal sequence (consisting of oligonucleotide (i) or oligonucleotide (ii)), e.g. to improve the activity of the polymerase used, are identified herein as Pol primers. These primers have the added advantage of allowing the start of RNA polymerases to synthesize RNA species. Thereby, such primers allow the amplification of target nucleic acid sequences as RNA molecules. Said RNA molecules can be used in RNA amplification systems, such as NASBA™ (nucleic acid sequence based amplification).

The NASBA method (see Kievits et al., 1991) is an isothermal method for the amplification of target RNA or DNA accomplished by the simultaneous enzymatic activity of a reverse transcriptase such as AMV reverse transcriptase, an RNA polymerase such as T7 RNA polymerase, and an RNase such as RNase H. For example, an RNA NASBA comprises an extension of a forward (or backward) primer which contains a T7, T3 or SP6 promoter sequence by reverse transcriptase (RT) on an RNA/DNA template, degradation of the RNA strand by RNase H (or heat denaturation for dsDNA which is formed in the case of a DNA NASBA), synthesis of a second DNA strand by a backward (or forward) primer extension with AMV-RT and RNA synthesis by T7, T3 or SP6 RNA polymerase. With RNA synthesis, the system enters the cyclic phase which is based on the above principles.

For HPV detection purposes, the forward primers can be either Pol GP5+ or Pol GP6+ primers while GP6+ and GP5+, respectively, can be used as the backward primers.

The invention also provides an oligonucleotide selected from the group consisting of (v) the 25-mer 5'-GAAAAATAAACTGTAAATCATATTC-3' (SEQ ID NO:2) or the 25-mer which is complementary to SEQ ID NO:2;

(vi) a 25-mer derived from (iv) by from 1 to 5 nucleotide substitutions;

(vii) a 25⁺-mer having a 3' terminal sequence consisting of (iv) or (v);

(viii) the 28-mer 5'-GAAAAATAAACTGTAAATCATATTCTTC-3' (SEQ ID NO:10) or the 28-mer which is complementary to SEQ ID NO:10;

(ix) the 28-mer 5'-GAAAAATAAACTGTAAATCATATTCCTC-3' (SEQ ID NO:18) or the 28-mer which is complementary to SEQ ID NO:18;

(x) a 28-mer derived from (vii) or (viii) by from 1 to 5 nucleotide substitutions;

(xi) a 28⁺-mer having a 3' terminal sequence consisting of (vii), (viii) or (ix);

(xii) a fragment of (v), (vi), (viii), (ix) or (x) having a length of from 8 to 18 nucleotides.

The oligonucleotide (v) is derived from a relatively conserved part of the L1 region of HPV. The 25-mer of SEQ ID NO:2 is composed of primer GP6, as described in WO91/10675, and an extension at the 3' terminus of the five additional nucleotides TATTC. In view of this 3' extension, it is referred to herein as GP6+.

The invention includes the complementary sequence, which may be useful in nucleic acid amplification methods such as the LCR.

The same applies to fragments having a length of from 8 to 18 nucleotides.

The oligonucleotide (vi) is derived from SEQ ID NO:2 or from its complementary sequence by from 1 to 5 nucleotide substitutions. Preferably, as in the case of oligonucleotide (ii), said substitutions concern substitutions occurring between different HPV strains. For example, the 11th nucleotide (C) is substituted in many strains by T (in HPV6B, HPV13, HPV31, HPV39, HPV42, HPV51, HPV52, HPV53 and HPV56). The 21st nucleotide (T) is substituted by A in several strains (in HPV11, HPV13, HPV31 and HPV52). The 23rd nucleotide (T) is substituted by C in several strains (in HPV6B, HPV11, HPV39 and HPV51). Therefore, the invention covers oligonucleotides containing these, and similar substitutions, such as, for example, the 25-mers:

| | |
|---|---|
| 5'-GAAAAATAAACTGTAAATCAAATTC-3' | (SEQ ID NO:3) |
| 5'-GAAAAATAAACTGTAAATCATACTC-3' | (SEQ ID NO:4) |
| 5'-GAAAAATAAACTGTAAATCAAACTC-3' | (SEQ ID NO:5) |
| 5'-GAAAAATAAATTGTAAATCATATTC-3' | (SEQ ID NO:6) |
| 5'-GAAAAATAAATTGTAAATCAAATTC-3' | (SEQ ID NO:7) |
| 5'-GAAAAATAAATTGTAAATCATACTC-3' | (SEQ ID NO:8) |
| 5'-GAAAAATAAATTGTAAATCAAACTC-3' | (SEQ ID NO:9) |

Preferably, however, nucleotide substitutions which give rise to self-annealing of the oligonucleotide molecules are avoided, as explained above for oligonucleotide (ii).

Oligonucleotide (viii) is the 28-mer of SEQ ID NO:10 which is composed of SEQ ID NO:2 and a 3' extension consisting of the three nucleotides TTC, or the complementary sequence of SEQ ID NO:10, and oligonucleotide (ix) is the 28-mer of SEQ ID NO:18 which is composed of SEQ ID NO:2 and a 3' extension consisting of the three nucleotides CTC, or the complementary sequence of SEQ ID NO:18. The additional extension at the 3'-end is possible because the relevant conserved part of the L1 region encompasses a further glutamic acid codon.

The oligonucleotide (x) is derived from SEQ ID NO:10, or from its complementary sequence, or from SEQ ID NO:18, or from its complementary sequence, by from 1 to 5 nucleotide substitutions. Preferably, as in the case of oligonucleotides (ii) and (vi), said substitutions concern substitutions occurring between different HPV strains. Examples of oligonucleotide (x) are:

5'-GAAAAATAAACTGTAAATCATATTCTTC-3'(SEQ ID NO:10)

5'-GAAAAATAAACTGTAAATCAAATTCTTC-3'(SEQ ID NO:11)

5'-GAAAAATAAACTGTAAATCATACTCTTC-3'(SEQ ID NO:12)

5'-GAAAAATAAACTGTAAATCAAAC TCTTC-3' (SEQ ID NO:13)

5'-GAAAAATAAATTGTAAATCATATTCTTC-3' (SEQ ID NO:14)

5'-GAAAAATAAATTGTAAATCAAATTCTTC-3'(SEQ ID NO:15)

5'-GAAAAATAAATTGTAAATCATACTCTTC-3'(SEQ ID NO:16)

5'-GAAAAATAAATTGTAAATCAAAC TCTTC-3' (SEQ ID NO:17)

5'-GAAAAATAAACTGTAAATCATATTCCTC-3'(SEQ ID NO:18)

5'-GAAAAATAAACTGTAAATCAAA TTCCTC-3' (SEQ ID NO:19)

5'-GAAAAATAAACTGTAAATCATACTCCTC-3'(SEQ ID NO:20)

5'-GAAAAATAAACTGTAAATCAAAC TCCTC-3' (SEQ ID NO:21)

5'-GAAAAATAAATTGTAAATCATATTCCTC-3' (SEQ ID NO:22)

5'-GAAAAATAAATTGTAAATCAAATTCCTC-3'(SEQ ID NO:23)

5'-GAAAAATAAATTGTAAATCATACTCCTC-3'(SEQ ID NO:24)

5'-GAAAAATAAATTGTAAATCAAAC TCCTC-3' (SEQ ID NO:25)

Oligonucleotide (vii) is a 25+-mer having a 3' terminal sequence consisting of (v) or (vi); and oligonucleotide (xi) is a 28+-mer having a 3' terminal sequence consisting of (viii), (ix) or (x). As in the case of oligonucleotide (iii), the extension at the 5'-end may have any length, but the total length of the oligonucleotide is preferably kept at 50 nucleotides at most, more preferably at not more than 40 nucleotides. It is preferred that the extension at the 5'-end comprises one or more restriction sites (Res primers) or a promoter sequence (Pol primers).

The invention further provides a pair of primers for use in a nucleic acid amplification process, such as PCR or NASBA, for the amplification of DNA of genital HPV genotypes, wherein the first primer consists of an oligonucleotide selected from the group consisting of (i), (ii) and (iii), and the second primer consists of an oligonucleotide selected from the group consisting of (v), (vi), (vii), (viii), (ix), (x) and (xi).

The invention also provides a primer set for use in a nucleic acid amplification process, such as LCR, for the amplification of DNA of genital HPV genotypes, wherein a first primer consists of an oligonucleotide selected from the group consisting of (i), (ii), (iii), (iv), (v), (vi), (vii), (viii), (ix), (x), (xi) and (xii), a second primer consists of an oligonucleotide complementary to said first primer, a third primer consists of an oligonucleotide corresponding to a region in the HPV genome substantially adjacent to the region from which said first primer is derived, and a fourth primer consists of an oligonucleotide which is complementary to said third primer.

The invention is further embodied in a method of amplifying DNA of genital HPV genotypes by means of a nucleic acid amplification process, comprising using a primer consisting of an oligonucleotide selected from the group consisting of (i), (ii), (iii), (iv), (v), (vi), (vii), (viii), (ix), (x), (xi) and (xii).

More particularly, the invention provides a method of amplifying DNA of genital HPV genotypes by means of a PCR using a pair of primers wherein a first primer consists of an oligonucleotide selected from the group consisting of (i), (ii) and (iii), and the second primer consists of an oligonucleotide selected from the group consisting of (v), (vi), (vii), (viii), (ix), (x) and (xi).

Similarly, the invention provides a method of amplifying DNA of genital HPV genotypes by means of a NASBA, using a pair of primers wherein a first primer consists of an oligonucleotide selected from the group consisting of (i), (ii) and (iii), and the second primer consists of an oligonucleotide selected from the group consisting of (v), (vi), (vii), (viii), (ix), (x) and (xi), with the proviso that one of the primers has a 5'-end which comprises a promoter sequence.

Also, the invention provides a method of amplifying DNA of genital HPV genotypes by means of an LCR, using a set of primers which comprises a first primer consisting of an oligonucleotide selected from the group consisting of (i), (ii), (iii), (iv), (v), (vi), (vii), (viii), (ix), (x), (xi) and (xii), a second primer consisting of an oligonucleotide which is complementary to the first primer, a third primer which consists of an oligonucleotide corresponding to a region in the HPV genome substantially adjacent to the region from which the first primer is derived, and a fourth primer consisting of an oligonucleotide which is complementary to the third primer.

The invention is also embodied in a method of analysing a sample, such as a cervical smear, for the presence therein of genital HPV genotypes which comprises amplifying DNA of a genital HPV present in the sample by means of a nucleic acid amplification process, employing a primer consisting of an oligonucleotide selected from the group consisting of (i), (ii), (iii), (iv), (v), (vi), (vii), (viii), (ix), (x), (xi) and (xii), and subsequently detecting a product of the amplification. Again, the nucleic acid amplification process may consist of, e.g., PCR, NASBA or LCR. The primers to be used in the amplification process should be appropriately chosen, depending on the kind of amplification process.

According to the invention, the primer annealing step in the nucleic acid amplification process is carried out preferably at a temperature of 30–50° C., more preferably at a temperature of 35–45° C., most preferably at a temperature of 38–42° C.

Further, according to the invention, the nucleic acid amplification process is preferably carried out at a $Mg^{2+}$ concentration of 2–10 mM, more preferably at a $Mg^{2+}$ concentration of 2.5–5 mM, most preferably at a $Mg^{2+}$ concentration of 3.0–4.0 mM.

According to the invention, the optimum results are obtained at an annealing temperature of about 40° C. (normally 55° C.) and at a $Mg^{2+}$ concentration of about 3.5 mM (normally 1.5 mM $Mg^{2+}$).

The new primers according to the invention enable the detection not only of genital HPV types whose sequence is already known, but also of HPV types whose sequence is (as yet) unknown and even of new HPV types.

According to the invention, it is preferred to adopt the general strategy for screening cervical smears which has been disclosed in WO91/10675. Said strategy is based on the combined use of HPV general primers according to the invention and the previously described HPV type-specific anticontamination primers. The procedure of this PCR strategy is described in WO91/10675 which has been incorporated herein by reference.

According to another aspect of this invention, the product of the amplification is detected by means of a DNA hybridization process using HPV type-specific oligonucleotide probes, the oligonucleotides of the probes being selected from the group consisting of:

5'-ATCCGTAACTACATCTTCCACATACACCAA-3', (SEQ ID NO:29), specific for HPV-6; (a)

5'-ATCTGTGTCTAAATCTGCTACATACACTAA-3', (SEQ ID NO:30), specific for HPV-11; (b)

5'-GTCATTATGTGCTGCCATATCTACTTCAGA-3', (SEQ ID NO:31), specific for HPV-16; (c)

5'-TGCTTCTACACAGTCTCCTGTACCTGGGCA-3', (SEQ ID NO:32), specific for HPV-18; (d)

5'-AGTACATTATCTGCAGCATCTGCATCCACT-3', (SEQ ID NO:33), specific for HPV-26; (e)

5'-TGTTTGTGCTGCAATTGCAAACAGTGATAC-3', (SEQ ID NO:34), specific for HPV-31; (f)

5'-TTTATGCACACAAGTAACTAGTGACAGTAC-3', (SEQ ID NO:35), specific for HPV-33; (g)

5'-TACACAATCCACAAGTACAAATGCACCATA-3', (SEQ ID NO:36), specofic for HPV-34; (h)

5'-GTCTGTGTGTTCTGCTGTGTCTTCTAGTGA-3', (SEQ ID NO:37), specific for HPV-35; (i)

5'-TCTACCTCTATAGAGTCTTCCATACCTTCT-3', (SEQ ID NO:38), specific for HPV-39; (j)

5'-GCTGCCACACAGTCCCCCACACCAACCCCA-3', (SEQ ID NO:39), specific for HPV-40; (k)

5'-CTGCAACATCTGGTGATACATATACAGCTG-3', (SEQ ID NO:40), specific for HPV-42; (l)

5'-TCTACTGACCCTACTGTGCCCAGTACATAT-3', (SEQ ID NO:41), specific for HPV-43; (m)

5'-GCCACTACACAGTCCCCTCCGTCTACATAT-3', (SEQ ID NO:42), specific for HPV-44; (n)

5'-ACACAAAATCCTGTGCCAAGTACATATGAC-3', (SEQ ID NO:43), specific for HPV-45; (o)

5'-AGCACTGCCACTGCTGCGGTTTCCCCAACA-3', (SEQ ID NO:44), specific for HPV-51; (p)

5'-TGCTGAGGTTAAAAAGGAAAGCACATATAA-3', (SEQ ID NO:45), specific for HPV-52; (q)

5'-TACAGCATCCACGCAGGATAGCTTTAATAA-3', (SEQ ID NO:46), specific for HPV-54; (r)

5'-GTACTGCTACAGAACAGTTAAGTAAATATG-3', (SEQ ID NO:47), specific for HPV-56; (s)

5'-ATTATGCACTGAAGTAACTAAGGAAGGTAC-3', (SEQ ID NO:48), specific for HPV-58; (t)

5'-TCTACTACTGCTTCTATTCCTAATGTATAC-3', (SEQ ID NO:49), specific for HPV-59; (u)

5'-TACTGCTACATCCCCCCCTGTATCTGAATA-3', (SEQ ID NO:50), specific for HPV-61; (v)

5'-TATTAATGCAGCTAAAAGCACATTAACTAA-3', (SEQ ID NO:51), specific for HPV-66; (w)

5'-TCTACTACTACTGAATCAGCTGTACCAAAT-3', (SEQ ID NO:52), specific for ME180; (x)

and the oligonucleotides complementary to these sequences.

In a preferred embodiment of the method, said HPV type-specific oligonucleotide probes are applied in the form of two separate probe mixtures, one mixture containing probes specific for HPV types 16, 18, 31, 33, 35, 39, 45, 51, 52, 54, 56 and 58, and not containing probes specific for HPV types 6, 11, 34, 40, 42, 43 and 44, and the other mixture containing probes specific for HPV types 6, 11, 34, 40, 42, 43 and 44, and not containing probes specific for HPV types 16, 18, 31, 33, 35, 39, 45, 51, 52, 54, 56 and 58.

According to the above preferred embodiment, the HPV high risk probe mixture contains up to 12 different HPV-specific oligonucleotide probes, preferably all 12. The mixture is not necessarily complete, however, and it may be advisable to add type-specific probes for other high risk HPV types, such as HPV 59, HPV66 and ME180. The preferred HPV low risk probe mixture as shown above contains up to 7 different HPV-specific oligonucleotide probes, preferably all 7. The composition of this low risk HPV probe mixture is certainly incomplete, however, because only those HPV types are included which are frequently present in the Dutch population. Therefore, both the high risk and the low risk probe cocktails need to be supplemented in future when new identified high risk HPVs and frequently present low risk HPVs are found. Especially the cocktail probe detecting the high risk HPVs is very important for cervical cancer screening and should therefore be as complete as possible.

It is preferred but not required to use probe mixtures. Instead, it is also possible to use the individual probes separately. Although it seems most practical to compose one high risk and one low risk cocktail probe, it is also possible to prepare e.g. two different high risk probe mixtures which together cover all high risk HPV types. The same can be done with the low risk cocktail probe: it can be divided over two (or more) different probe mixtures.

Although the probes can carry any suitable probe label, such as radioactive labels, enzyme labels, fluorescent labels, etc., they preferably comprise digoxygenine as a label.

The invention is furthermore embodied in a HPV type-specific oligonucleotide probe useful in a method as described above, the oligonucleotide of the probe being selected from the group consisting of:

5'-ATCCGTAACTACATCTTCCACATACACCAA-3', (SEQ ID NO:29), specific for HPV-6; (a)

5'-ATCTGTGTCTAAATCTGCTACATACACTAA-3', (SEQ ID NO:30), specific for HPV-11; (b)

5'-GTCATTATGTGCTGCCATATCTACTTCAGA-3', (SEQ ID NO:31), specific for HPV-16; (c)

5'-TGCTTCTACACAGTCTCCTGTACCTGGGCA-3', (SEQ ID NO:32), specific for HPV-18; (d)

5'-AGTACATTATCTGCAGCATCTGCATCCACT-3', (SEQ ID NO:33), specific for HPV-26; (e)

5'-TGTTTGTGCTGCAATTGCAAACAGTGATAC-3', (SEQ ID NO:34), specific for HPV-31; (f)

5'-TTTATGCACACAAGTAACTAGTGACAGTAC-3', (SEQ ID NO:35), specific for HPV-33; (g)

5'-TACACAATCCACAAGTACAAATGCACCATA-3', (SEQ ID NO:36), specific for HPV-34; (h)

5'-GTCTGTGTGTTCTGCTGTGTCTTCTAGTGA-3', (SEQ ID NO:37), specific for HPV-35; (i)

5'-TCTACCTCTATAGAGTCTTCCATACCTTCT-3', (SEQ ID NO:38), specific for HPV-39; (j)

5'-GCTGCCACACAGTCCCCCACACCAACCCCA-3', (SEQ ID NO:39), specific for HPV-40; (k)

5'-CTGCAACATCTGGTGATACATATACAGCTG-3', (SEQ ID NO:40), specific for HPV-42; (l)

5'-TCTACTGACCCTACTGTGCCCAGTACATAT-3', (SEQ ID NO:41), specific for HPV-43; (m)

5'-GCCACTACACAGTCCCCTCCGTCTACATAT-3', (SEQ ID NO:42), for HPV-44; (n)

5'-ACACAAAATCCTGTGCCAAGTACATATGAC-3', (SEQ ID NO:43), for HPV-45; (o)

5'-AGCACTGCCACTGCTGCGGTTTCCCCAACA-3', (SEQ ID NO:44), for HPV-51; (p)

5'-TGCTGAGGTTAAAAAGGAAAGCACATATAA-3', (SEQ ID NO:45), for HPV-52; (q)

5'-TACAGCATCCACGCAGGATAGCTTTAATAA-3', (SEQ ID NO:46), for HPV-54; (r)

5'-GTACTGCTACAGAACAGTTAAGTAAATATG-3', (SEQ ID NO:47), for HPV-56; (s)

5'-ATTATGCACTGAAGTAACTAAGGAAGGTAC-3', (SEQ ID NO:48), for HPV-58; (t)

5'-TCTACTACTGCTTCTATTCCTAATGTATAC-3', (SEQ ID NO:49), for HPV-59; (u)

5'-TACTGCTACATCCCCCCCTGTATCTGAATA-3', (SEQ ID NO:50), for HPV-61; (v)

5'-TATTAATGCAGCTAAAAGCACATTAACTAA-3', (SEQ ID NO:51), for HPV-66; (w)

5'-TCTACTACTACTGAATCAGCTGTACCAAAT-3', (SEQ ID NO:52), for ME180; (x)

and the oligonucleotides complementary to these sequences.

The invention also includes a HPV high risk cocktail probe which is a mixture of oligonucleotide probes useful in the above method, said mixture containing probes specific for HPV types 16, 18, 31, 33, 35, 39, 45, 51, 52, 54, 56 and 58, and not containing probes specific for HPV types 6, 11, 34, 40, 42, 43 and 44. As discussed above, the high risk cocktail probe is preferably as complete as possible and therefore preferably contains probes for further high risk HPV types. The high risk probe mixture may be presented as one complete mixture, or alternatively as two or more different probe mixtures which together cover the high risk HPV types as completely as possible.

The invention also includes a HPV low risk cocktail probe which is a mixture of oligonucleotide probes useful in the above method, said mixture containing probes specific for HPV types 6, 11, 34, 40, 42, 43 and 44, and not containing probes specific for HPV types 16, 18, 31, 33, 35, 39, 45, 51, 52, 54, 56 and 58. The observations made above in connection with the high risk cocktail probe are valid also for the low risk cocktail probe.

The invention also includes an assembly of a HPV high risk cocktail probe and a HPV low risk cocktail probe, said assembly comprising a mixture containing probes specific for HPV types 16, 18, 31, 33, 35, 39, 45, 51, 52, 54, 56 and 58, and not containing probes specific for HPV types 6, 11, 34, 40, 42, 43 and 44, said assembly further comprising a mixture containing probes specific for HPV types 6, 11, 34, 40, 42, 43 and 44, and not containing probes specific for HPV types 16, 18, 31, 33, 35, 39, 45, 51, 52, 54, 56 and 58.

The invention will now be illustrated by the following examples which are preceded by materials and methods used therein. The examples are merely intended for illustrative purposes and not to restrict the scope of the invention.

MATERIALS AND METHODS

HPV Clones and Cervical Scrapes

HPV clones of types 6b, 11, 16, 18 and 30 were kindly provided by Drs. H. zur Hausen and L. Gissmann (Heidelberg, Germany), HPV types 13, 32 and 40 by Dr. E.-M. De Villiers (Heidelberg, Germany), 31 and 35 by Dr. A. Lorincz (Gaithersburg, Md.); 33, 39, 54, 55 and 66 by Dr. G. Orth (Paris, France), 45 by Dr. K. V. Shah (Baltimore, Md.), 51 by Dr. G. Nuovo (New York, N.Y.), and 59 by Dr. T. Matsukura (Tokyo, Japan). Cloned HPV types 43 and 56 were obtained from the American Type Culture Collection (Rockville, Md.). The MY11/09 (Manos et al., 1989) directed PCR products of HPV types 52 and 58, which include the GP5/6 region, were cloned in our laboratory from cervical scrapes and verified by sequence comparison.

A total of 264 cervical scrapes collected from 222 women were subjected to HPV PCR. These women participate in a prospective follow-up study to relate HPV presence and morphology of cervical cells with the clinical behaviour of cervical lesions. Both, for HPV detection and cytomorphological analysis, two cervical scrapes were taken. The first was used for cytomorphological examination. Cytomorphological classification was done according to a slight modification of the Pap procedure as used in the Netherlands (Vooijs, 1987; modified KOPAC classification, briefly: Pap I, normal cells; Pap II, inflammation; Pap IIIa, mild and moderate dysplasia; Pap IIIb, severe dysplasia; Pap IV, carcinoma in situ; Pap V, invasive cancer). The scrapes analysed included cases of Pap I (n=120), Pap II (n=73), Pap IIIa (n=59), and Pap IIIb (n=12). Cells remaining from the first spatula and from the second scrape were collected in phosphate-buffered saline containing 0.05% mertiolate (Van den Brule et al., 1991; Walboomers et al., 1992). The scrapes were pretreated according to a freeze-thaw heating protocol as described previously (van den Brule et al., 1990b). Briefly, cells were spun down for 10 min at 3000 g and resuspended in 1 ml of 10 mM Tris-HCl pH 8.1. For each PCR 10 µl aliquots were transferred to a new reaction tube containing a screw cap (Sarstedt, Etten-Leur, the Netherlands). Aliquots were stored at −70° C. followed by thawing at room temperature. Subsequently, aliquots were heated for 5 min at 100° C. and after cooling on ice (10 min) centrifuged for 1 min at 3000 g.

Primer Design and Synthesis

HPV DNA homology studies were performed with PC/Gene (IntelliGenetics, Inc., Release 6.7) using the CLUSTAL computer program (Higgins and Sharp, 1988) for multiple sequence alignment. Sequences of the L1 region of 23 mucosotropic HPV genotypes, as derived from the EMBL database or kindly provided by Dr. H. Delius, Heidelberg, Germany, were used to modify the original GP5 and GP6 primers which span a region of approximately 150 bp. Primer sequences are shown in Tables 1A/1B and primers were commercially synthesized by Applied Biosystems (Perkin-Elmer Nederland B. V., The Netherlands) using the methoxyphosphoramidite method.

Polymerase Chain Reaction

General primer-mediated PCR (Snijders et al., 1990) was performed on cloned HPV DNAs mixed with 100 ng human placental DNA or 10 µl of the crude cell suspensions of cervical scrapes. All cervical scrapes appeared positive after pre-screening by PCR using β-globin specific primers (Saiki et al., 1985), indicating a proper quality of the samples.

GP5/6 and GP5+/6+ PCR assays were performed under the same conditions. The reaction mixtures of 50 µl contained 50 mM KCl, 10 mM Tris HCl pH 8.3, 200 µM of each dNTP, 3.5 mM MgCl$_2$, 1 unit of thermostable DNA polymerase (Amplitaq; Perkin Elmer Cetus) and 50 pmol of each primer of the GP5/6 or GP5+/6+ primer combination. The mixture was overlaid with several drops of paraffin oil and incubated for 5 minutes at 94° C. for DNA denaturation, followed by 40 cycles of amplification using a PCR processor (Bio-med, Theres, Germany). Each cycle included a denaturation step to 94° C. for 1 min, an annealing step to 40° C. for 2 min and a chain elongation step to 72° C. for 1.5 min. To ensure complete extension of the amplified DNA, the final elongation step was prolonged by 4 min.

The GP-PCR products were analyzed as previously described (van den Brule et al., 1990b; Walboomers et al., 1992) by gel electrophoresis followed by diffusion blotting and low stringent Southern blot hybridisation with a cocktail probe consisting of HPV6, HPV11, HPV16, HPV18, HPV31 and HPV33 specific GP-PCR products.

Type-specific PCR for HPV6, HPV11, HPV16, HPV18, HPV31 and HPV33 was performed using combinations of HPV6, HPV16, HPV33 and HPV11, HPV18, HPV31 specific primers as described by Van den Brule et al. (1990). PCR conditions were the same as described for the GP-PCR, except that 25 pmol of each primer, 1.5 mM MgCl$_2$, and an annealing temperature of 55° C. were used.

EXAMPLE 1
Design of GP5+ and GP6+ Primers

Previously, alignment of putative amino acid sequences from the L1 region flanked by both GP5 and GP6 of 24 mucosotropic HPVs has revealed the consensus sequences ThrArgSerThrAsn (TRSTN) immediately downstream of the GP5 (forward primer) region and ArgHisXGluGlu (RHXEE) upstream of the GP6 (backward primer) region (Van den Brule et al., 1992). Since these amino acid conservations reflect codon conservations at the nucleotide level, part of these sequences could be used to elongate both GP5 and GP6 at their 3'-ends. In order to ensure that the 3'-ends of the primers completely match HPV target sequences, efforts were made to add sequences including at least two unambiguously conserved nucleotides at the 3' terminus of the elongated GP5 and GP6.

Sequence comparison of the 3' boundary of the GP5 region of 23 mucosotropic HPV genotypes revealed conserved nucleotides encoding the amino acid sequence ThrThrArg, of which the first two nucleotides (CA) encoding the first threonine are included in GP5 (Table 1A). For GP5 modification, a T residue (third nucleotide position of this first threonine codon corresponding to the HPV16 sequence) and the first two invariable nucleotides (CA) encoding the second threonine were added to the 3'-end of GP5. Further elongation of GP5 was hampered by the fact that the arginine residue can be encoded by six different codons, and consequently both the first and the third nucleotides of this codon are variable.

The complementary sequences of the 3' boundary of the GP6 region of 23 mucosotropic HPVs revealed nucleotide sequences encoding the amino acid consensus GluGluTyr/Phe, of which the third nucleotide encoding tyrosine/phenylalanine is included in GP6 (Table 1B). For GP6 modification, five nucleotides were added to the 3' primer end. In this way the complementary sequences of the two 3' terminal nucleotides of the modified primer represent the invariable bases (GA) encoding glutamic acid.

Primer sequences of the elongated 23-mer GP5 (named GP5+) and 25-mer GP6 (named GP6+), aligned with corresponding sequences of the L1 region of 20 mucosotropic HPV genotypes are indicated in Table 1.

EXAMPLE 2
PCR Experiments
1. Use of Elongated GP5/6 Primers (GP5+/6+) in a Model System of Cloned HPV DNAs The GP5/6 and GP5+/6+ PCR assays were compared on cloned HPV DNA. Reconstructions consisting of 1 ng of DNA of the mucosotropic HPV types HPV6, HPV11, HPV13, HPV16, HPV18, HPV30, HPV31, HPV32, HPV33, HPV35, HPV39, HPV40, HPV43, HPV45, HPV51, HPV52, HPV54, HPV55, HPV56, HPV58, HPV59 and HPV66 mixed with 100 ng of human placenta DNA were used for this purpose.

A successful amplification was obtained for all HPV genotypes with both general primer PCR assays. However, only weak bands could be detected after gel electrophoresis of the GP5/6 PCR products of HPV30, HPV32, HPV39, HPV51 and HPV66. This reduction in DNA amplification efficiency could also be observed after low stringency hybridisation of the GP5/6 PCR products of HPV genotypes HPV30, HPV32, HPV39 and HPV66 with a HPV-specific cocktail probe. In contrast, strong positive signals were generated with the elongated pimer pair GP5+/6+ both after gel electrophoresis and hybridisation. Furthermore, GP5/6 amplification in general gave rise to enhanced levels of cellular background signals compared to the GP5+/GP6+ PCR. The lack of non-specific binding of the GP5+ and GP6+ may contribute to an enhanced HPV DNA detection level.

The sensitivity of the GP5/6 and GP5+/6+ PCR assays was compared by subjecting different concentrations of cloned DNA of HPV16, HPV39 and HPV51 diluted in human placental DNA to both assays. These HPV types were selected because they show varying numbers (2, 6 and 9, respectively) of mismatches with the GP5/6 primers, which could influence the sensitivity range of the primers.

It appeared that HPV16 could be detected with GP5+/6+ at a 10-fold higher sensitivity compared with GP5/6. After hybridisation of the HPV16 GP5+/6+ products with a HPV cocktail probe a detection level of 1 fg of cloned HPV16 DNA in a background of 100 ng human placental DNA could be detected. This corresponds to approximately 70 copies of viral genome per 20,000 cells.

HPV39 and HPV51 could be detected at a 10- to 100-fold increased sensitivity with the elongated general primers as compared to the GP5/6. However, these HPV genotypes still could be detected at a lower sensitivity than HPV16. HPV39 and HPV51 both could be detected at the 10 pg level. A sensitivity level of approximately 700,000 copies of viral DNA per 20,000 cells was observed for these types using the GP5+/6+ combination.

2. Evaluation of the GP5+/6+ PCR on Cell Lines and Cytomorphologically Normal Cervical Scrapes Four cervical carcinoma cell lines and 100 cervical scrapes were subjected to both the GP5/6 and GP5+/6+ PCR assay.

The GP5/6 and GP5+/6+primer pairs were used to amplify 100 ng of the HPV16 containing cervical carcinoma cell lines Siha and CaSki and the HPV18 cervical carcinoma cell lines C4-1 and HeLa.

The low HPV copy number cell lines such as Siha (1–10 copies), C4-1 (1–5 copies) and HeLa (10–50 copies) were less efficiently amplified in the GP5/6 PCR than in the GP5+/6+ PCR. The CaSki cell line (500 copies) seemed to be equally efficiently amplified with both general primer pairs.

After gel electrophoresis, GP5+/6+ PCR products of all four cell lines tested could be visualized. Hybridisation of these amplification products with a HPV cocktail probe resulted in strong positive signals with all cell lines tested as expected. Additionally, the same background signals were obtained for HPV18 in the GP5/6 PCR as observed for HPV18 in the cloned HPV reconstruction experiment. This phenomenon was not found with the GP5+/6+ primer pair.

Further clinical evaluation of the novel GP-PCR assay was carried out by screening 100 cytomorphologically normal cervical scrapes which appeared negative in the GP5/6 PCR assay. Additional HPV positivity could be detected with the GP5+/6+ PCR for seven GP5/6 PCR-negative cervical scrapes. Stringent successive hybridisation with HPV type-specific probes and (automatic) sequencing were used to identify the HPV types detected by GP5+/GP6+ PCR but not by GP5/6 PCR. HPV30, HPV32, HPV39 (2×) and HPV66 could be detected. Also, two potentially novel types could be detected with the elongated general primers.

3. Comparison of Different GP6+ Primers

Reconstruction experiments using as the second primer either the oligonucleotide SEQ ID NO:2 or the oligonucleotide SEQ ID NO:4 revealed identical efficiency of these two different GP6+ primers.

4. Discussion of the Results

Since a small number of cervical scrapes displayed ambiguous results and some of the mucosotropic HPV genotypes showed a decreased sensitivity with the GP5/6 PCR, possibilities for optimization of this HPV detection assay were evaluated. It has been found that sufficient primer length and a perfect 3' primer end homology are crucial for efficient DNA polymerase binding and the formation of a stabile primer/template complex. Also, since the GP5/6 adjacent regions are highly conserved within the mucosotropic HPV group, it might turn out to be feasible to enhance the GP5/6 PCR efficiency by elongation of the original GP5/6 primers at their 3'-ends by 3 and 5 basepairs, respectively.

Indeed, elongation of the GP5/6 primers resulted in an enhanced HPV detection level as was proven by comparison of both primer pairs on cloned HPVs and clinical samples. All HPV types tested with the GP5+/6+ primers could be detected with a higher sensitivity. However, even types like HPV57 are detected at a very low sensitivity which cannot be explained by the high number of mismatches as compared to the general primers (GP5/6: 8 mismatches; GP5+/6+: 9 mismatches).

Remarkably it appeared from our results that even after the introduction of more mismatches between target and primer DNA (for example compare HPV39 with GP6 (2 mismatches) and with GP6+ (3 mismatches)) the sensitivity increased after application of the elongated primers. This indicates that under the conditions used the number of mismatches is not absolutely critical for an efficient PCR.

In general, background signals as were seen with the original GP5/6 PCR were not detected with the elongated general primers which might at least partially explain the enhanced sensitivity as found with the GP5+/6+. Apart from the enhanced sensitivity the GP5+/6+ assay also showed indications to detect HPV in a more universal way. This is reflected by the enhanced detection of HPV types HPV30, HPV32, HPV39 and HPV66 as well as with a more enhanced sensitivity of detecting for example HPV39 and HPV51 (showing a lot of mismatches with GP5/6) compared with HPV16.

The strength of the new system was further substantiated by screening cytomorphologically normal cervical scrapes of a well-defined patient population with both GP-PCR assays. This resulted in a slightly higher prevalence rate with the elongated general primers. When analysing the additionally detected HPV genotypes it was found that these were high and low risk types.

Additionally, two supposedly novel HPV genotypes were detected. The result of additional HPV detection in cytomorphologically normal scrapes indicate that the prevalence of oncogenic HPV types has to be raised to about 5%. In addition, GP5+/6+ primers could be of great value to detect potentially novel HPV types in extragenital sites, e.g. the aerodigestive tract. Therefore, the improved general primer system, GP5+/6+, could be of great value in HPV research.

In general we can conclude that the GP5+/6+ primers can detect mucosotropic HPV genotypes in a more sensitive and a more universal manner, compared to the GP5/GP6 primers.

EXAMPLE 3

Use of HPV Type-specific Probes

1. Selection of Type-specific HPV Oligoprobes Within the GP5+/6+ Region

Multiple alignment of GP5/6 sequences of HPVs was performed using the CLUSTAL computer program (PC/Gene, Release 6.7; IntelliGenetics, Inc). Regions of heterogeneity (van den Brule et al., 1992) were used for the selection of oligonucleotides (30-mers) specific for HPV 6, 11, 16, 18, 26, 31, 33, 34, 35, 39, 40, 42, 43, 44, 45, 51, 52, 54, 56, 58, 59, 61, 66 and ME180 (for nucleotide sequence see Table 2). To predetermine the specificity of these internal oligonucleotides, they were aligned using the QSEARCH program (PC/Gene) to 71 papillomavirus (PV)-specific nucleotide sequences containing the L1 open reading frame (ORF) specific GP5/6 region. This group of sequences consisted of 61 complete sequenced cloned HPV genomes and sequenced PCR products (GP- or MY-PCR) of known HPVs, 3 sequenced GP-PCR products of still unidentified HPVs (HPV-X) and 7 sequences were of non-human origin. Most of the oligonucleotides contained more than 6 mismatches to the other HPV sequences. Only the HPV 40-specific oligonucleotide had less than 5 mismatches with one of the PV types analysed (4 mismatches with HPV 7). With the allowance of 10 mismatches in the alignment, significantly more oligonucleotides (n=15) aligned with other HPV sequences (n=30). When 15 mismatches (50% of the oligonucleotide) are allowed during the sequence comparison, the number of homologies between the oligoprobes and PV sequences was enormous. Furthermore, it was excluded by sequence analysis that oligoprobes when used in a mixture could crosshybridise to each other.

2. Labeling of Oligoprobes

Type-specific oligonucleotides (30-mers) were synthesized by Pharmacia (Sweden) using the methoxyphosphoramidite method. Digoxygenin-11-ddUTP (DIG) labeling of 100 pmol of each oligonucleotide by using terminal transferase (Boehringer Mannheim, Germany) was performed according to the manufacturers protocol. The relative concentration of each labeled oligonucleotide was estimated using a spotblot to be able to include similar amounts of each probe in the cocktail.

3. Southern Blot Analysis of HPV-specific PCR Products

Each membrane was prehybridised for 2 hours in hybridisation mix containing 5*SSC, 0.02% SDS and 0.1% sarkosyl (1*SSC is 0.15M sodium chloride/0.015M sodium citrate; SDS is sodium dodecyl sulphate). Subsequently, the membranes were hybridised with different DIG-labeled oligonucleotides (100 pmol probe/25 ml hybridisation mix), or with a cocktail of DIG-labeled oligoprobes. Hybridisations were performed overnight at 55° C. The membranes were washed three times at 55° C. for 30 minutes in 3*SSC, 0.5% SDS. Detection of DIG-labeled oligonucleotides was accomplished by a chemiluminescence process using Lumigen™-PPD according to the manufacturers protocol (Boehringer Mannheim, Germany). Subsequently, the membranes were exposed for 60 min at room temperature to Kodak Royal X-Omat films. In addition, some membranes were also hybridised with $\alpha^{32}P$ dCTP labeled probe of GP-PCR products derived from cloned sequenced HPV types 6, 11, 16, 18, 31 and 33 as described by van den Brule et al. (1990b). Autoradiography was performed for 18 hours at −70° C. with Kodak Royal X-Omat film and intensifying screens.

4. Specificity of the DIG-labeled HPV Type-specific Oligoprobes

The specificities of the oligonucleotide probes in PCR for the HPVs 6, 11, 16, 18, 26, 31, 33, 34, 35, 39, 40, 42, 43, 44, 45, 51, 52, 54, 56, 58, 61 and ME180 were experimentally determined by Southern blot analysis. For this purpose membranes containing approximately 100 pg GP-PCR products of the HPV test panel (HPV 6, 11, 34, 40, 42, 43, 44, 16, 18, 31, 33, 35, 39, 45, 51, 52, 54, 56, 58, 59 and 66) were hybridised to different oligonucleotides. All probes appeared to be specific for their relevant HPV genotype and no crosshybridisation with other HPV types was observed when used at 55° C. It was demonstrated that the selected oligonucleotide probes did not show crosshybridisation even at high amplimer copynumber and could be used for specific HPV typing.

5. Sensitivity of DIG Oligoprobe Hybridisation

For a selected number of HPVs the sensitivity of the oligoprobe hybridisation was determined by Southern blot analysis after 10-fold dilutions of the corresponding HPV GP5+/6+ PCR products. HPV types were chosen which are easy (HPV 6, 16, 18, 42, 45, 51) or difficult (HPV 35, 39) to amplify by GP5+/6+ PCR. For some of these types (HPV 6, 16, 18) the corresponding PCR product is present in the routineously used random primer labeled cocktail probe. For most probes a detection level of 1 ng of PCR products was found. Membranes were also hybridised with either the high risk or low risk cocktail probe in order to compare the performance of the type-specific oligoprobes individually and when used in a mixture of oligoprobes. It was found that the sensitivities of the digoxygenine-labeled oligoprobes did not decrease (significantly) when used in a cocktail. The sensitivities of the individual digoxygenine-labeled oligoprobes and the DIG cocktail probes were also compared with the random primer labeled $\alpha^{32}P$ dCTP GP5+/6+ PCR product probe till now routineously used in our laboratory. It appeared that the overall sensitivity of DIG-labeled oligoprobes is comparable to the labeled $\alpha^{32}P$ dCTP GP-PCR product probe.

6. HPV Detection

Either 1 ng DNA of a cloned HPV or 10 μl of crude cell suspensions of cervical scrapes were subjected to GP5+/6+ PCR as described previously by De Roda Husman et al. (1994b). Briefly, PCR reactions were carried out in 50 μl containing 50 mM KCl, 10 mM Tris HCl pH 8.3, 200 μM of each dNTP, 3.5 mM $MgCl_2$, 1 unit of thermostabile DNA polymerase (Amplitaq; Cetus, USA) and 25 pmol of the GP5+ and GP6+ primer. Five minutes at 94° C. for DNA denaturation was followed by 40 cycles of amplification using a PCR processor (PE9600; Cetus, USA). Each cycle included a denaturation step at 94° C. for 1 minute, a primer annealing step at 40° C. for 2 minutes and a chain elongation step at 72° C. for 1.5 minutes. The final elongation step was prolonged by 4 minutes to ensure a complete extension of the amplified DNA. Samples with equal intensity at the gel level were selected for further testing. A total of 5 μl of the PCR products of these samples were layered in 25-fold on 1.5% agarose gels and transferred onto positively charged nylon membranes (Qiabrane, Westburg) by diffusion blotting in 0.5N NaOH, 0.6M NaCl.

7. Analysis of HPV High and Low Risk DIG-labeled Cocktail Probes

Having established the specificity and sensitivity of the HPV type-specific DIG oligoprobes, the group-specific cocktail probes were prepared and checked for their performance on GP5+/6+ PCR products on a panel of HPV types. The high risk HPV cocktail probe was prepared by adding together 100 pmol of the following DIG-labeled oligoprobes: 16, 18, 31, 33, 35, 39, 45, 51, 52, 54, 56, 58 and 68. The low risk HPV cocktail probe consists of 100 pmol of the probes 6, 11, 34, 40, 42, 43 and 44. It appeared that both group-specific HPV cocktail probes clearly identified the high risk respectively low risk HPV genotypes. Furthermore, as expected no crosshybridisation could be detected.

TABLE 1A

Sequence comparison of GP5 and GP5+

|  |  |  |
|---|---|---|
|  | Th rTh rArg |  |
| GP5 | 5'-TTTGTTACTGTGGTAGATAC-3' | (SEQ ID NO: 54) |
| GP5+ | 5'-TTTGTTACTGTGGTAGATAC TAC-3' | (SEQ ID NO: 55) |
| HPV6B | .................... C.. ACGC |  |
| HPV11 | .................... C.. .... |  |
| HPV13 | ...........A..T..... ... .... |  |
| HPV16 | ...........A..T..... ... .... |  |
| HPV18 | .................... C.. T... |  |
| HPV30 | ........T..G...C.. C.. TA.G |  |
| HPV31 | .................... C.. ...T |  |
| HPV32 | ...C.A.....T..G..... ... C..T |  |
| HPV33 | ...........T........ C.. T... |  |
| HPV34 | ...T.A.....T........ ... TA.A |  |
| HPV35 | ...........A..T..... A.. C..T |  |
| HPV39 | ...C........T..G..C.. ... C..T |  |
| HPV40 | ........A..T.....C.. C.. T..T |  |
| HPV42 | ...T.A........T..... ... C..T |  |
| HPV45 | ...........A..G..C.. ... C... |  |
| HPV51 | ...A....CTGT...T..... ... CA.A |  |

TABLE 1A-continued

Sequence comparison of GP5 and GP5+

| | | |
|---|---|---|
| HPV52 | .....C..A..T..G..... | C.. T..T |
| HPV53 | .....A.....T..G..... | C.. CA.G |
| HPV56 | ..........A......... | ... TA.A |
| HPV58 | ........C.....T..... | C.. T..T |
| HPV61 | .....A..C..T..G..... | C.. C... |
| HPV66 | ...........T..G..... | ... CA.A |
| ME180 | ...C........T..G..... | C.. T... |

TABLE 1B

Sequence comparison of GP6 and GP6+

```
            Glu GluTy r
                Ph  e
GP6             3'-ACTAAATGTCAAATAAAAAG-5'    (SEQ ID NO: 56)
GP6+    3'-CTTAT ACTAAATGTCAAATAAAAAG-5'      (SEQ ID NO: 57)
HPV6B   CTT ..C... ..........T..........
HPV11   ..C ..C.A ....................
HPV13   ... ....A ..........T..........
HPV16   ..C ..... ....................
HPV18   ..C ..... ......C.............
HPV30   ..C ..... ...T.........C.C....
HPV31   ..C ....A ..........T.....T....
HPV32   ..C ..... ....T..........T....
HPV33   ... ..... ...G........C......
HPV34   ... ..C.. ...GG.C......C.C....
HPV35   ... ..... ....................
HPV39   ..C ..C.. ..........T.....T....
HPV40   ..C ..C.A ......C.............
HPV42   ... ..... ....C.C..T.....T....
HPV45   ..C ..... ....................
HPV51   ... ..C.. ...T..C..T..........
HPV52   ..C ....A ..........T..........
HPV53   ..C ..... ...T.....T...C.C....
HPV56   ..C ..... ...T.....T....C.....
HPV58   ... ..... ...G........C......
HPV61   ..C ..C.A ......C..T..........
HPV66   ..C ..... ...TG........C.C....
ME180   ..C ..... ......C..T.....T....
```

TABLE 2

Sequences of HPV type-specific probes

| Sequence | specific for: | SEQ ID NO: |
|---|---|---|
| ATCCGTAACTACATCTTCCACATACACCAA | HPV-6 | 29 |
| ATCTGTGTCTAAATCTGCTACATACACTAA | HPV-11 | 30 |
| GTCATTATGTGCTGCCATATCTACTTCAGA | HPV-16 | 31 |
| TGCTTCTACACAGTCTCCTGTACCTGGGCA | HPV-18 | 32 |
| AGTACATTATCTGCAGCATCTGCATCCACT | HPV-26 | 33 |
| TGTTTGTGCTGCAATTGCAAACAGTGATAC | HPV-31 | 34 |
| TTTATGCACACAAGTAACTAGTGACAGTAC | HPV-33 | 35 |
| TACACAATCCACAAGTACAAATGCACCATA | HPV-34 | 36 |
| GTCTGTGTGTTCTGCTGTGTCTTCTAGTGA | HPV-35 | 37 |
| TCTACCTCTATAGAGTCTTCCATACCTTCT | HPV-39 | 38 |
| GCTGCCACACAGTCCCCCACACCAACCCCA | HPV-40 | 39 |
| CTGCAACATCTGGTGATACATATACAGCTG | HPV-42 | 40 |
| TCTACTGACCCTACTGTGCCCAGTACATAT | HPV-43 | 41 |
| GCCACTACACAGTCCCCTCCGTCTACATAT | HPV-44 | 42 |
| ACACAAAATCCTGTGCCAAGTACATATGAC | HPV-45 | 43 |
| AGCACTGCCACTGCTGCGGTTTCCCCAACA | HPV-51 | 44 |
| TGCTGAGGTTAAAAAGGAAAGCACATATAA | HPV-52 | 45 |
| TACAGCATCCACGGATAGCTTTAATAA | HPV-54 | 46 |
| GTACTGCTACAGAACAGTTAAGTAAATATG | HPV-56 | 47 |
| ATTATGCACTGAAGTAACTAAGGAAGGTAC | HPV-58 | 48 |
| TCTACTACTGCTTCTATTCCTAATGTATAC | HPV-59 | 49 |
| TACTGCTACATCCCCCCCTGTATCTGAATA | HPV-61 | 50 |
| TATTAATGCAGCTAAAAGCACATTAACTAA | HPV-66 | 51 |
| TCTACTACTACTGAATCAGCTGTACCAAAT | ME180 | 52 |

REFERENCES

Barany, F. (1991) Genetic disease detection and DNA amplification using cloned thermostable ligase. Proc. Natl. Acad. Sci. USA 88: 189–193.

Boshart, M., Gissmann, L., Ikenberg, H., Kleinheinz, A., Scheurlen, W., zur Hausen, H. (1984) A new type of papillomavirus DNA, its presence in genital cancer biopsies and in cell lines derived from cervical cancer. EMBO J 3: 1151–1157.

De Roda Husman, A.-M., Walboomers, J. M. M., Meijer, C. J. L. M., Risse, E. K. J., Schipper, M. E. I., Helmerhorst, T. M., Bleker, O. P., Delius, H., van den Brule, A. J. C. and Snijders, P. J. F. (1994a) Analysis of cytomorphologically abnormal cervical scrapes for the presence of 27 mucosotropic human papillomavirus genotypes, using polymerase chain reaction. Int. J. Cancer 56: 802–806.

De Roda Husman, A.-M., Walboomers, J. M. M., van den Brule, A. J. C., Meijer, C. J. L. M., and Snijders, P. J. F. (1994b) The use of general primers GP5 and GP6 elongated at the 3' ends with adjacent highly conserved sequences improves human papillomavirus detection. Submitted for publication.

De Villiers, E.-M. (1989) Heterogeneity in the human papillomavirus group. J. Virol. 63: 4898–4903.

De Villiers, E.-M., Hirsch-Benan, A., von Knebel-Doeberitz, C., Neumann, C. and zur Hausen, H. (1989) Two newly identified human papillomavirus types (HPV 40 and 57) isolated from mucosal lesions. Virology 171: 248–253.

Evander, M. and Wadell, G. (1991) A general primer pair for amplification and detection of genital human papillomavirus types. J. Virol. Methods 31: 239–250.

Grégoire, L., Arella, M., Campione-Piccardo, J. and Lancaster, W. D. (1989) Amplification of human papillomavirus DNA sequences by using conserved primers. J. Clin. Microbiol. 27: 2660–2665.

Kievits, T., van Gemen, B., van Strijp, D., Schukkink, R., Dircks, M., Adriaanse, H., Malek, L., Sooknanan, R. and Lens, P. (1991) NASBA™ isothermal enzymatic in vitro nucleic acid amplification optimized for the diagnosis of HIV I infection. J. Med. Virol. 35: 273–286.

Mack, D. H. and Sninsky, J. J. (1988) A sensitive method for the identification of uncharacterized viruses related to known virus groups: Hepadnavirus model system. Proc. Natl. Acad. Sci. USA 85: 6977–6981.

Manos, M. M., Ting, Y., Wright, D. K., Lewis, A. J., Broker, T. R. and Wolinsky, S. M. (1989) Use of polymerase chain reaction amplification for the detection of genital human papillomaviruses. Cancer cells 7: 209–214.

Melkert, P. W. J., Hopman, E., Van den Brule, A. J. C., Risse, E. K. J., van Diest, P. J., Bleker, O. P., Helmerhorst, Th., Schipper, M. E. I., Meijer, C. J. L. M. and Walboomers, J. M. M. (1993) Prevalence of HPV in cytomorphologically normal smears, as determined by the polymerase chain reaction, is age-dependent. Int. J. Cancer 53: 919–923.

Newton, C. R., Graham, A., Heptinstall, L. E., Powell, S. J., Summers, C., Kalsheker, N., Smith, J. C. and Markham, A. F. (1989) Analysis of any point mutation in DNA. The amplification refractory mutation system (ARMS). Nucl. Acids Res. 17: 2503–2516.

Saiki, R. K., Scharf, S., Faloona, F., Mullis, K. B., Horn, G. T., Erlich, H. A. and Arnheim, N. (1985) Enzymatic amplification of beta-globin genomic sequences and restriction site analysis for diagnosis of sickle-cell anemia. Science 230: 1350–1354.

Schwarz, E., Freese, U. K., Gissmann, L., Mayer, W., Roggenbuck, B., Stremlau, A. and Zur Hausen, H. (1985) Structure and transcription of human papilloma virus sequences in cervical carcinoma cells. EMBO J. 2: 2341–2348.

Snijders, P. J. F., van den Brule, A. J. C., Schrijnemakers, H. F. J., Snow, G., Meijer, C. J. L. M. and Walboomers, J. M. M. (1990) The use of general primers in the polymerase chain reaction permits the detection of a broad spectrum of human papillomavirus genotypes. J. Gen. Virol. 71: 173–181.

Sommer, R. and Tautz, D. (1989) Minimal homology requirements for PCR primers. Nucl. Acids Res. 17: 6749.

Van den Brule, A. J. C., Claas, E. C. J., du Maine, M., Melchers, W. J. G., Helmerhorst, T., Quint, W. G. V., Lindeman, J., Meijer, C. J. L. M. and Walboomers, J. M. M. (1989) The use of anti-contamination primers in the polymerase chain reaction for the detection of human papilloma virus genotypes in cervical scrapes and biopsies. J. Med. Virol. 29: 20–27.

Van den Brule, A. J. C., Snijders, P. J. F., Gordijn, R. L. J., Bleker, O. P., Meijer, C. J. L. M. and Walboomers, J. M. M. (1990a) General primer polymerase chain reaction permits the detection of sequenced and still unsequenced human papillomavirus genotypes in cervical scrapes and carcinomas. Int. J. Cancer 45: 644–649.

Van den Brule, A. J. C., Meijer, C. J. L. M., Bakels, V., Kenemans, P. and Walboomers, J. M. M. (1990b) Rapid detection of human papillomavirus in cervical scrapes by combined general primer-mediated and type-specific polymerase chain reaction. J. Clin. Microbiol. 28: 2739–2743.

Van den Brule, A. J. C., Walboomers, J. M. M., Du Maine, M., Kenemans, P. and Meijer, C. J. L. M. (1991) Difference in prevalence of human papillomavirus genotypes in cytomorphologically normal cervical smears is associated with a history of cervical intraepithelial neoplasia. Int. J. Cancer 48: 404–408.

Van den Brule, A. J. C., Snijders, P. J. F., Raaphorst, P. M. C., Schrijnemakers, H. F. J., Delius, H., Gissmann, L., Meijer, C. J. L. M. and Walboomers, J. M. M. (1992) General primer polymerase chain reaction in combination with sequence analysis for identification of potentially novel human papillomavirus geno-types in cervical lesions. J. Clin. Microbiol. 30: 1716–1721.

Yee, C., Krishnan-Hewlett, I., Baker, C. C., Schlegel, R. and Howley, P. M. (1985) Presence and expression of human papillomavirus sequences in human cervical carcinoma cell lines. Am. J. Pathol. 119: 361–366.

Zur Hausen, H. (1991) Human papillomaviruses in the pathogenesis of anogenital cancer. Virology 184: 9–13.

What is claimed is:

1. A general primer for amplification and detection of genital HPV genotypes, which is an oligonucleotide selected from the group consisting of:
   (i) the 23-mer 5'-TTTGTTACTGTGGTAGATACTAC-3' (SEQ ID NO:1) or a 23-mer which is fully complementary to SEQ ID NO:1;
   (ii) a 23-mer which differs from (i) by from 1 to 5 nucleotide substitutions at sites where nucleotide substitutions occur between different HPV strains but with the exclusion of substitutions of the last two nucleotides at the 3' end; and
   (iii) a 23⁺-mer having a 3' terminal sequence consisting of (i) or (ii).

2. A primer according to claim 1 which is the 23-mer 5'-TTTGTTACTGTGGTAGATACTAC-3' (SEQ ID NO:1) or a 23-mer which is fully complementary to SEQ ID NO:1.

3. A primer according to claim 1 which is a 23-mer which differs from (i) by from 1 to 5 nucleotide substitutions occurring between different HPV strains but with the exclusion of substitutions of the last two nucleotides at the 3' end.

4. A primer according to claim 1 which is a 23⁺-mer having a 3' terminal sequence consisting of (i) or (ii), wherein the 5'-end comprises a restriction site.

5. A primer according to claim 1 which is a 23⁺-mer having a 3' terminal sequence consisting of (i) or (ii), wherein the 5'-end comprises a promoter sequence.

6. A primer according to claim 1 which contains no more than 50 nucleotides.

7. A general primer for amplification and detection of genital HPV genotypes, which is an oligonucleotide selected from the group consisting of:
   (i) the 25-mer 5'-GAAAAATAAACTGTAAATCATATTC-3' (SEQ ID NO: 2) or a 25-mer which is fully complementary to SEQ ID NO:2;
   (ii) a 25-mer which differs from (i) by from 1 to 5 nucleotide substitutions at sites where nucleotide substitutions occur between different HPV strains but with the exclusion of substitutions of the last two nucleotides at the 3' end;
   (iii) a 25⁺-mer having a 3' terminal sequence consisting of (i) or (ii);
   (iv) the 28-mer 5'-GAAAAATAAACTGTAAATCATATTCTTC-3' (SEQ ID NO:10) or a 28-mer which is fully complementary to SEQ ID NO:10;
   (v) the 28-mer 5'-GAAAAATAAACTGTAAATCATATTCCTC-3' (SEQ ID NO:18) or a 28-mer which is fully complementary to SEQ ID NO:18;
   (vi) a 28-mer which differs from (iv) or (v) by from 1 to 5 nucleotide substitutions at sites where nucleotide substitutions occur between different HPV strains but with the exclusion of substitutions of the last two nucleotides at the 3' end; and
   (vii) a 28⁺-mer having a 3' terminal sequence consisting of (iv), (v) or (vi).

8. A primer according to claim 7 which is selected from the group consisting of:
   the 25-mer 5'-GAAAAATAAACTGTAAATCATATTC-3' (SEQ ID NO:2) or a 25-mer which is fully complementary to SEQ ID NO:2;
   the 28-mer 5'-GAAAAATAAACTGTAAATCATATTCTTC-3' (SEQ ID NO:10) or a 28-mer which is fully complementary to SEQ ID NO:10; and
   the 28-mer 5'-GAAAAATAAACTGTAAATCATATTCCTC-3' (SEQ ID NO:18) or a 28-mer which is fully complementary to SEQ ID NO:18.

9. A primer according to claim 7 which is selected from the group consisting of:
   a 25-mer which differs from (i) by from 1 to 5 nucleotide substitutions occurring between different HPV strains but with the exclusion of substitutions of the last two nucleotides at the 3' end; and
   a 28-mer which differs from (iv) or (v) by from 1 to 5 nucleotide substitutions occurring between different HPV strains but with the exclusion of substitutions of the last two nucleotides at the 3' end.

10. A primer according to claim 7 selected from the group consisting of:

| Sequence | SEQ ID |
|---|---|
| 5'-GAAAAATAAACTGTAAATCAAATTC-3' | (SEQ ID NO:3); |
| 5'-GAAAAATAAACTGTAAATCATACTC-3' | (SEQ ID NO:4); |
| 5'-GAAAAATAAACTGTAAATCAAACTC-3' | (SEQ ID NO:5); |
| 5'-GAAAAATAAATTGTAAATCATATTC-3' | (SEQ ID NO:6); |
| 5'-GAAAAATAAATTGTAAATCAAATTC-3' | (SEQ ID NO:7); |
| 5'-GAAAAATAAATTGTAAATCATACTC-3' | (SEQ ID NO:8); |
| 5'-GAAAAATAAATTGTAAATCAAACTC-3' | (SEQ ID NO:9); |
| 5'-GAAAAATAAACTGTAAATCATATTCTTC-3' | (SEQ ID NO:10); |
| 5'-GAAAAATAAACTGTAAATCAAATTCTTC-3' | (SEQ ID NO:11); |
| 5'-GAAAAATAAACTGTAAATCATACTCTTC-3' | (SEQ ID NO:12); |
| 5'-GAAAAATAAACTGTAAATCAAACTCTTC-3' | (SEQ ID NO:13); |

5'-GAAAAATAAATTGTAAATCATATTCTTC-3'(SEQ ID NO:14);
5'-GAAAAATAAATTGTAAATCAAATTCTTC-3' (SEQ ID NO:15);
5'-GAAAAATAAATTGTAAATCATACTCTTC-3' (SEQ ID NO:16);
5'-GAAAAATAAATTGTAAATCAAACTCTTC-3' (SEQ ID NO:17);
5'-GAAAAATAAACTGTAAATCATATTCCTC-3' (SEQ ID NO:18);
5'-GAAAAATAAACTGTAAATCAAATTCCTC-3' (SEQ ID NO:19);
5'-GAAAAATAAACTGTAAATCATACTCCTC-3' (SEQ ID NO:20);
5'-GAAAAATAAACTGTAAATCAAACTCCTC-3' (SEQ ID NO:21);
5'-GAAAAATAAATTGTAAATCATATTCCTC-3'(SEQ ID NO:22);
5'-GAAAAATAAATTGTAAATCAAATTCCTC-3' (SEQ ID NO:23);
5'-GAAAAATAAATTGTAAATCATACTCCTC-3' (SEQ ID NO:24);
5'-GAAAAATAAATTGTAAATCAAACTCCTC-3' (SEQ ID NO:25), and an oligonucleotide fully complementary to any one of these sequences.

11. A primer according to claim 7 which is a 25+-mer having a 3' terminal sequence consisting of (i) or (ii), or a 28+-mer having a 3' terminal sequence consisting of (iv), (v) or (vi), wherein the 5'-end comprises a restriction site.

12. A primer according to claim 7 which is a 25+-mer having a 3' terminal sequence consisting of (i) or (ii), or a 28+-mer having a 3' terminal sequence consisting of (iv), (v) or (vi), wherein the 5'-end comprises a promoter sequence.

13. A primer according to claim 7 which contains no more than 50 nucleotides.

14. A general primer pair for use in a nucleic acid amplification process for the amplification of DNA of genital HPV genotypes, wherein a first general primer consists of an oligonucleotide selected from the group consisting of:
   (i) the 23-mer 5'-TTTGTTACTGTGGTAGATACTAC-3' (SEQ ID NO:1) or a 23-mer which is fully complementary to SEQ ID NO:1;
   (ii) a 23-mer which differs from (i) by from 1 to 5 nucleotide substitutions at sites where nucleotide substitutions occur between different HPV strains but with the exclusion of substitutions of the last two nucleotides at the 3' end; and
   (iii) a 23+-mer having a 3' terminal sequence consisting of (i) or (ii);
and the second general primer consists of an oligonucleotide selected from the group consisting of:
   (iv) the 25-mer 5'-GAAAAATAAACTGTAAATCATATTC-3' (SEQ ID NO: 2) or a 25-mer which is fully complementary to SEQ ID NO:2;
   (v) a 25-mer which differs from (iv) by from 1 to 5 nucleotide substitutions at sites where nucleotide substitutions occur between different HPV strains but with the exclusion of substitutions of the last two nucleotides at the 3' end;
   (vi) a 25+-mer having a 3' terminal sequence consisting of (iv) or (v);
   (vii) the 28-mer 5'-GAAAAATAAACTGTAAATCATATTCTTC-3' (SEQ ID NO:10) or a 28-mer which is fully complementary to SEQ ID NO:10;
   (viii) the 28-mer 5-GAAAAATAAACTGTAAATCATATTCCTC-3' (SEQ ID NO:18) or a 28-mer which is fully complementary to SEQ ID NO:18;
   (ix) a 28-mer which differs from (vii) or (viii) by from 1 to 5 nucleotide substitutions at sites where nucleotide substitutions occur between different HPV strains but with the exclusion of substitutions of the last two nucleotides at the 3' end; and
   (x) a 28+-mer having a 3' terminal sequence consisting of (vii), (viii) or (ix).

15. A method of amplifying DNA of genital HPV genotypes comprising carrying out a nucleic acid amplification process using one or more general primers consisting of an oligonucleotide selected from the group consisting of:
   (i) the 23-mer 5'-TTTGTTACTGTGGTAGATACTAC-3' (SEQ ID NO:1) or a 23-mer which is fully complementary to SEQ ID NO:1;
   (ii) a 23-mer which differs from (i) by from 1 to 5 nucleotide substitutions at sites where nucleotide substitutions occur between different HPV strains but with the exclusion of substitutions of the last two nucleotides at the 3' end;
   (iii) a 23+-mer having a 3' terminal sequence consisting of (i) or (ii);
   (iv) the 25-mer 5'-GAAAAATAAACTGTAAATCATATTC-3' (SEQ ID NO: 2) or a 25-mer which is fully complementary to SEQ ID NO:2;
   (v) a 25-mer which differs from (iv) by from 1 to 5 nucleotide substitutions at sites where nucleotide substitutions occur between different HPV strains but with the exclusion of substitutions of the last two nucleotides at the 3' end;
   (vi) a 25+-mer having a 3' terminal sequence consisting of (iv) or (v);
   (vii) the 28-mer 5'-GAAAAATAAACTGTAAATCATATTCTTC-3' (SEQ ID NO:10) or a 28-mer which is fully complementary to SEQ ID NO:10;
   (viii) the 28-mer 5-GAAAAATAAACTGTAAATCATATTCCTC-3' (SEQ ID NO:18) or a 28-mer which is fully complementary to SEQ ID NO:18;
   (ix) a 28-mer which differs from (vii) or (viii) by from 1 to 5 nucleotide substitutions at sites where nucleotide substitutions occur between different HPV strains but with the exclusion of substitutions of the last two nucleotides at the 3' end; and
   (x) a 28+-mer having a 3' terminal sequence consisting of (vii), (viii) or (ix).

16. A method of amplifying DNA of genital HPV genotypes comprising carrying out a nucleic acid amplification process using a pair of general primers wherein a first primer consists of an oligonucleotide selected from the group consisting of:
   (i) the 23-mer 5'-TTTGTTACTGTGGTAGATACTAC-3' (SEQ ID NO:1) or a 23-mer which is fully complementary to SEQ ID NO:1;
   (ii) a 23-mer which differs from (i) by from 1 to 5 nucleotide substitutions at sites where nucleotide substitutions occur between different HPV strains but with the exclusion of substitutions of the last two nucleotides at the 3' end; and
   (iii) a 23+-mer having a 3' terminal sequence consisting of (i) or (ii);

and the second primer consists of an oligonucleotide selected from the group consisting of:

(iv) the 25-mer 5'-GAAAAATAAACTGTAAATCATATTC-3' (SEQ ID NO: 2) or a 25-mer which is fully complementary to SEQ ID NO:2;

(v) a 25-mer which differs from (iv) by from 1 to 5 nucleotide substitutions at sites where nucleotide substitutions occur between different HPV strains but with the exclusion of substitutions of the last two nucleotides at the 3' end;

(vi) a 25+-mer having a 3' terminal sequence consisting of (iv) or (v);

(vii) the 28-mer 5'-GAAAAATAAACTGTAAATCATATTCTTC-3' (SEQ ID NO:10) or a 28-mer which is fully complementary to SEQ ID NO:10;

(viii) the 28-mer 5'-GAAAAATAAACTGTAAATCATATTCCTC-3' (SEQ ID NO:18) or a 28-mer which is fully complementary to SEQ ID NO:18;

(ix) a 28-mer which differs from (vii) or (viii) by from 1 to 5 nucleotide substitutions at sites where nucleotide substitutions occur between different HPV strains but with the exclusion of substitutions of the last two nucleotides at the 3' end; and (x) a 28+-mer having a 3' terminal sequence consisting of (vii), (viii) or (ix).

17. A method of amplifying DNA of genital HPV genotypes comprising carrying out a nucleic acid amplification process using a pair of general primers wherein a first primer consists of an oligonucleotide selected from the group consisting of:

(i) the 23-mer 5'-TTTGTTACTGTGGTAGATACTAC-3' (SEQ ID NO:1) or a 23-mer which is fully complementary to SEQ ID NO:1;

(ii) a 23-mer which differs from (i) by from 1 to 5 nucleotide substitutions at sites where nucleotide substitutions occur between different HPV strains but with the exclusion of substitutions of the last two nucleotides at the 3' end; and (iii) a 23+-mer having a 3' terminal sequence consisting of (i) or (ii);

and the second primer consists of an oligonucleotide selected from the group consisting of:

(iv) the 25-mer 5'-GAAAAATAAACTGTAAATCATATTC-3' (SEQ ID NO: 2) or a 25-mer which is fully complementary to SEQ ID NO:2;

(v) a 25-mer which differs from (iv) by from 1 to 5 nucleotide substitutions at sites where nucleotide substitutions occur between different HPV strains but with the exclusion of substitutions of the last two nucleotides at the 3' end;

(vi) a 25+-mer having a 3' terminal sequence consisting of (iv) or (v);

(vii) the 28-mer 5'-GAAAAATAAACTGTAAATCATATTCTTC-3' (SEQ ID NO:10) or a 28-mer which is fully complementary to SEQ ID NO:10;

(viii) the 28-mer 5'-GAAAAATAAACTGTAAATCATATTCCTC-3' (SEQ ID NO:18) or a 28-mer which is fully complementary to SEQ ID NO:18;

(ix) a 28-mer which differs from (vii) or (viii) by from 1 to 5 nucleotide substitutions at sites where nucleotide substitutions occur between different HPV strains but with the exclusion of substitutions of the last two nucleotides at the 3' end; and (x) a 28+-mer having a 3' terminal sequence consisting of (vii), (viii) or (ix), with the proviso that one of the primers has a 5'-end which comprises a promoter sequence.

18. A method according to claim 15 wherein the nucleic acid amplification process comprises a primer annealing step which is carried out at a temperature of 30–50° C.

19. A method according to claim 15 wherein the nucleic acid amplification process is carried out at a $Mg^{2+}$ concentration of 2–10 mM.

20. A method of analyzing a sample for the presence therein of genital HPV genotypes which comprises amplifying DNA of a genital HPV present in the sample by means of a nucleic acid amplification process according to claim 15, and subsequently detecting a product of the amplification wherein the occurrence of amplification product indicates presence of a genital HPV genotype in the sample.

21. A method according to claim 20 wherein said sample is a cervical smear.

22. A method according to claim 20 wherein the product of the amplification is detected by means of a DNA hybridization process using HPV type-specific oligonucleotide probes, the probe(s) being selected from the group consisting of:

(a) 5'-ATCCGTAACTACATCTTCCACATACACCAA-3', specific for HPV-6;

(b) 5'-ATCTGTGTCTAAATCTGCTACATACACTAA-3', specific for HPV-11;

(c) 5'-GTCATTATGTGCTGCCATATCTACTTCAGA-3', specific for HPV-16;

(d) 5'-TGCTTCTACACAGTCTCCTGTACCTGGGCA-3', specific for HPV-18;

(e) 5'-AGTACATTATCTGCAGCATCTGCATCCACT-3', specific for HPV-26;

(f) 5'-TGTTTGTGCTGCAATTGCAAACAGTGATAC-3', specific for HPV-31;

(g) 5'-TTTATGCACACAAGTAACTAGTGACAGTAC-3', specific for HPV-33;

(h) 5'-TACACAATCCACAAGTACAAATGCACCATA-3', specific for HPV-34;

(i) 5'-GTCTGTGTGTTCTGCTGTGTCTTCTAGTGA-3', specific for HPV-35;

(j) 5'-TCTACCTCTATAGAGTCTTCCATACCTTCT-3', specific for HPV-39;

(k) 5'-GCTGCCACACAGTCCCCCACACCAACCCCA-3', specific for HPV-40;

(l) 5'-CTGCAACATCTGGTGATACATATACAGCTG-3', specific for HPV-42;

(m) 5'-TCTACTGACCCTACTGTGCCCAGTACATAT-3', specific for HPV-43;

(n) 5'-GCCACTACACAGTCCCCTCCGTCTACATAT-3', specific for HPV-44;

(o) 5'-ACACAAAATCCTGTGCCAAGTACATATGAC-3', specific for HPV-45;

(p) 5'-AGCACTGCCACTGCTGCGGTTTCCCCAACA-3', specific for HPV-51;

(q) 5'-TGCTGAGGTTAAAAAGGAAAGCACATATAA-3', specific for HPV-52;
(r) 5'-TACAGCATCCACGCAGGATAGCTTTAATAA-3', specific for HPV-54;
(s) 5'-GTACTGCTACAGAACAGTTAAGTAAATATG-3', specific for HPV-56;
(t) 5'-ATTATGCACTGAAGTAACTAAGGAAGGTAC-3', specific for HPV-58;
(u) 5'-TCTACTACTGCTTCTATTCCTAATGTATAC-3', specific for HPV-59;
(v) 5'-TACTGCTACATCCCCCCCTGTATCTGAATA-3', specific for HPV-61;
(w) 5'-TATTAATGCAGCTAAAAGCACATTAACTAA-3', specific for HPV-66;
(x) 5'-TCTACTACTACTGAATCAGCTGTACCAAAT-3', specific for ME180;

and an oligonucleotide fully complementary to any one of (a) to (x).

23. A method according to claim 22 wherein said HPV type-specific oligonucleotide probes are applied in the form of two separate probe mixtures, one mixture containing probes specific for all of the HPV types 16, 18, 31, 33, 35, 39, 45, 51, 52, 54, 56 and 58, and not containing probes specific for any of the HPV types 6, 11, 34, 40, 42, 43 and 44, and the other mixture containing probes specific for all of the HPV types 6, 11, 34, 40, 42, 43 and 44, and not containing probes specific for any of the HPV types 16, 18, 31, 33, 35, 39, 45, 51, 52, 54, 56 and 58.

24. A method according to claim 22 wherein said probes comprise digoxygenine as a label.

* * * * *

SEQUENCE LISTING (1) GENERAL INFORMATION:

(iii) NUMBER OF SEQUENCES: 57

(2) INFORMATION FOR SEQ ID NO: 1:

(i) SEQUENCE CHARACTERISTICS:
      (A) LENGTH: 23 base pairs

```
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (xi) SEQUENCE DESCRIPTION: SEQ ID NO: 1:

TTTGTTACTG TGGTAGATAC TAC                                              23

(2) INFORMATION FOR SEQ ID NO: 2:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (xi) SEQUENCE DESCRIPTION: SEQ ID NO: 2:

GAAAAATAAA CTGTAAATCA TATTC                                            25

(2) INFORMATION FOR SEQ ID NO: 3:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (xi) SEQUENCE DESCRIPTION: SEQ ID NO: 3:

GAAAAATAAA CTGTAAATCA AATTC                                            25

(2) INFORMATION FOR SEQ ID NO: 4:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (xi) SEQUENCE DESCRIPTION: SEQ ID NO: 4:

GAAAAATAAA CTGTAAATCA TACTC                                            25

(2) INFORMATION FOR SEQ ID NO: 5:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (xi) SEQUENCE DESCRIPTION: SEQ ID NO: 5:

GAAAAATAAA CTGTAAATCA AACTC                                            25
```

(2) INFORMATION FOR SEQ ID NO: 6:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (xi) SEQUENCE DESCRIPTION: SEQ ID NO: 6:

GAAAAATAAA TTGTAAATCA TATTC                                      25

(2) INFORMATION FOR SEQ ID NO: 7:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (xi) SEQUENCE DESCRIPTION: SEQ ID NO: 7:

GAAAAATAAA TTGTAAATCA AATTC                                      25

(2) INFORMATION FOR SEQ ID NO: 8:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (xi) SEQUENCE DESCRIPTION: SEQ ID NO: 8:

GAAAAATAAA TTGTAAATCA TACTC                                      25

(2) INFORMATION FOR SEQ ID NO: 9:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (xi) SEQUENCE DESCRIPTION: SEQ ID NO: 9:

GAAAAATAAA TTGTAAATCA AACTC                                      25

(2) INFORMATION FOR SEQ ID NO: 10:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (xi) SEQUENCE DESCRIPTION: SEQ ID NO: 10:

GAAAAATAAA CTGTAAATCA TATTCTTC                              28

(2) INFORMATION FOR SEQ ID NO: 11:

(i) SEQUENCE CHARACTERISTICS:
            (A) LENGTH: 28 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (xi) SEQUENCE DESCRIPTION: SEQ ID NO: 11:

GAAAAATAAA CTGTAAATCA AATTCTTC                              28

(2) INFORMATION FOR SEQ ID NO: 12:

(i) SEQUENCE CHARACTERISTICS:
            (A) LENGTH: 28 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (xi) SEQUENCE DESCRIPTION: SEQ ID NO: 12:

GAAAAATAAA CTGTAAATCA TACTCTTC                              28

(2) INFORMATION FOR SEQ ID NO: 13:

(i) SEQUENCE CHARACTERISTICS:
            (A) LENGTH: 28 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (xi) SEQUENCE DESCRIPTION: SEQ ID NO: 13:

GAAAAATAAA CTGTAAATCA AACTCTTC                              28

(2) INFORMATION FOR SEQ ID NO: 14:

(i) SEQUENCE CHARACTERISTICS:
            (A) LENGTH: 28 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (xi) SEQUENCE DESCRIPTION: SEQ ID NO: 14:

GAAAAATAAA TTGTAAATCA TATTCTTC                              28

(2) INFORMATION FOR SEQ ID NO: 15:

(i) SEQUENCE CHARACTERISTICS:
            (A) LENGTH: 28 base pairs (B) TYPE: nucleic acid
        (C) STRANDEDNESS: single
        (D) TOPOLOGY: linear (ii) MOLECULE TYPE: DNA (genomic)

(iii) HYPOTHETICAL: NO (xi) SEQUENCE DESCRIPTION: SEQ ID NO: 15:

GAAAAATAAA TTGTAAATCA AATTCTTC                                          28

(2) INFORMATION FOR SEQ ID NO: 16:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (xi) SEQUENCE DESCRIPTION: SEQ ID NO: 16:

GAAAAATAAA TTGTAAATCA TACTCTTC                                          28

(2) INFORMATION FOR SEQ ID NO: 17:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (xi) SEQUENCE DESCRIPTION: SEQ ID NO: 17:

GAAAAATAAA TTGTAAATCA AACTCTTC                                          28

(2) INFORMATION FOR SEQ ID NO: 18:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (xi) SEQUENCE DESCRIPTION: SEQ ID NO: 18:

GAAAAATAAA CTGTAAATCA TATTCCTC                                          28

(2) INFORMATION FOR SEQ ID NO: 19:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (xi) SEQUENCE DESCRIPTION: SEQ ID NO: 19:

GAAAAATAAA CTGTAAATCA AATTCCTC                                          28

(2) INFORMATION FOR SEQ ID NO: 20:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (xi) SEQUENCE DESCRIPTION: SEQ ID NO: 20:

GAAAAATAAA CTGTAAATCA TACTCCTC                           28

(2) INFORMATION FOR SEQ ID NO: 21:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (xi) SEQUENCE DESCRIPTION: SEQ ID NO: 21:

GAAAAATAAA CTGTAAATCA AACTCCTC                           28

(2) INFORMATION FOR SEQ ID NO: 22:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (xi) SEQUENCE DESCRIPTION: SEQ ID NO: 22:

GAAAAATAAA TTGTAAATCA TATTCCTC                           28

(2) INFORMATION FOR SEQ ID NO: 23:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (xi) SEQUENCE DESCRIPTION: SEQ ID NO: 23:

GAAAAATAAA TTGTAAATCA AATTCCTC                           28

(2) INFORMATION FOR SEQ ID NO: 24:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (xi) SEQUENCE DESCRIPTION: SEQ ID NO: 24:

GAAAAATAAA TTGTAAATCA TACTCCTC                                              28

(2) INFORMATION FOR SEQ ID NO: 25:

(i) SEQUENCE CHARACTERISTICS:
            (A) LENGTH: 28 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (xi) SEQUENCE DESCRIPTION: SEQ ID NO: 25:

GAAAAATAAA TTGTAAATCA AACTCCTC                                              28

(2) INFORMATION FOR SEQ ID NO: 26:

(i) SEQUENCE CHARACTERISTICS:
            (A) LENGTH: 28 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (xi) SEQUENCE DESCRIPTION: SEQ ID NO: 26:

AATTCTAATA CGACTCACTA TAGGGGGA                                              28

(2) INFORMATION FOR SEQ ID NO: 27:

(i) SEQUENCE CHARACTERISTICS:
            (A) LENGTH: 24 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (xi) SEQUENCE DESCRIPTION: SEQ ID NO: 27:

TTATTAACCC TCACTAAAGG GAAG                                                  24

(2) INFORMATION FOR SEQ ID NO: 28:

(i) SEQUENCE CHARACTERISTICS:
            (A) LENGTH: 23 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (xi) SEQUENCE DESCRIPTION: SEQ ID NO: 28:

ATTTAGGTGA CACTATAGAA TAC                                                   23

(2) INFORMATION FOR SEQ ID NO: 29:

(i) SEQUENCE CHARACTERISTICS:

(A) LENGTH: 30 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (xi) SEQUENCE DESCRIPTION: SEQ ID NO: 29:

ATCCGTAACT ACATCTTCCA CATACACCAA                                              30

(2) INFORMATION FOR SEQ ID NO: 30:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (xi) SEQUENCE DESCRIPTION: SEQ ID NO: 30:

ATCTGTGTCT AAATCTGCTA CATACACTAA                                              30

(2) INFORMATION FOR SEQ ID NO: 31:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (xi) SEQUENCE DESCRIPTION: SEQ ID NO: 31:

GTCATTATGT GCTGCCATAT CTACTTCAGA                                              30

(2) INFORMATION FOR SEQ ID NO: 32:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (xi) SEQUENCE DESCRIPTION: SEQ ID NO: 32:

TGCTTCTACA CAGTCTCCTG TACCTGGGCA                                              30

(2) INFORMATION FOR SEQ ID NO: 33:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (xi) SEQUENCE DESCRIPTION: SEQ ID NO: 33:

```
AGTACATTAT CTGCAGCATC TGCATCCACT                                30
```

(2) INFORMATION FOR SEQ ID NO: 34:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (xi) SEQUENCE DESCRIPTION: SEQ ID NO: 34:

```
TGTTTGTGCT GCAATTGCAA ACAGTGATAC                                30
```

(2) INFORMATION FOR SEQ ID NO: 35:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (xi) SEQUENCE DESCRIPTION: SEQ ID NO: 35:

```
TTTATGCACA CAAGTAACTA GTGACAGTAC                                30
```

(2) INFORMATION FOR SEQ ID NO: 36:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (xi) SEQUENCE DESCRIPTION: SEQ ID NO: 36:

```
TACACAATCC ACAAGTACAA ATGCACCATA                                30
```

(2) INFORMATION FOR SEQ ID NO: 37:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (xi) SEQUENCE DESCRIPTION: SEQ ID NO: 37:

```
GTCTGTGTGT TCTGCTGTGT CTTCTAGTGA                                30
```

(2) INFORMATION FOR SEQ ID NO: 38:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (xi) SEQUENCE DESCRIPTION: SEQ ID NO: 38:

TCTACCTCTA TAGAGTCTTC CATACCTTCT                    30

(2) INFORMATION FOR SEQ ID NO: 39:

(i) SEQUENCE CHARACTERISTICS:
            (A) LENGTH: 30 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (xi) SEQUENCE DESCRIPTION: SEQ ID NO: 39:

GCTGCCACAC AGTCCCCCAC ACCAACCCCA                    30

(2) INFORMATION FOR SEQ ID NO: 40:

(i) SEQUENCE CHARACTERISTICS:
            (A) LENGTH: 30 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (xi) SEQUENCE DESCRIPTION: SEQ ID NO: 40:

CTGCAACATC TGGTGATACA TATACAGCTG                    30

(2) INFORMATION FOR SEQ ID NO: 41:

(i) SEQUENCE CHARACTERISTICS:
            (A) LENGTH: 30 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (xi) SEQUENCE DESCRIPTION: SEQ ID NO: 41:

TCTACTGACC CTACTGTGCC CAGTACATAT                    30

(2) INFORMATION FOR SEQ ID NO: 42:

(i) SEQUENCE CHARACTERISTICS:
            (A) LENGTH: 30 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (xi) SEQUENCE DESCRIPTION: SEQ ID NO: 42:

GCCACTACAC AGTCCCCTCC GTCTACATAT                    30

(2) INFORMATION FOR SEQ ID NO: 43:

(i) SEQUENCE CHARACTERISTICS:
    (A) LENGTH: 30 base pairs
    (B) TYPE: nucleic acid
    (C) STRANDEDNESS: single
    (D) TOPOLOGY: linear (ii) MOLECULE TYPE: DNA (genomic)

(iii) HYPOTHETICAL: NO (xi) SEQUENCE DESCRIPTION: SEQ ID NO: 43:

ACACAAAATC CTGTGCCAAG TACATATGAC                                      30

(2) INFORMATION FOR SEQ ID NO: 44:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (xi) SEQUENCE DESCRIPTION: SEQ ID NO: 44:

AGCACTGCCA CTGCTGCGGT TTCCCCAACA                                      30

(2) INFORMATION FOR SEQ ID NO: 45:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (xi) SEQUENCE DESCRIPTION: SEQ ID NO: 45:

TGCTGAGGTT AAAAAGGAAA GCACATATAA                                      30

(2) INFORMATION FOR SEQ ID NO: 46:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (xi) SEQUENCE DESCRIPTION: SEQ ID NO: 46:

TACAGCATCC ACGCAGGATA GCTTTAATAA                                      30

(2) INFORMATION FOR SEQ ID NO: 47:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (xi) SEQUENCE DESCRIPTION: SEQ ID NO: 47:

GTACTGCTAC AGAACAGTTA AGTAAATATG                                30

(2) INFORMATION FOR SEQ ID NO: 48:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (xi) SEQUENCE DESCRIPTION: SEQ ID NO: 48:

ATTATGCACT GAAGTAACTA AGGAAGGTAC                                30

(2) INFORMATION FOR SEQ ID NO: 49:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (xi) SEQUENCE DESCRIPTION: SEQ ID NO: 49:

TCTACTACTG CTTCTATTCC TAATGTATAC                                30

(2) INFORMATION FOR SEQ ID NO: 50:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (xi) SEQUENCE DESCRIPTION: SEQ ID NO: 50:

TACTGCTACA TCCCCCCCTG TATCTGAATA                                30

(2) INFORMATION FOR SEQ ID NO: 51:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (xi) SEQUENCE DESCRIPTION: SEQ ID NO: 51:

TATTAATGCA GCTAAAAGCA CATTAACTAA                                30

(2) INFORMATION FOR SEQ ID NO: 52:

(i) SEQUENCE CHARACTERISTICS:
        (A) LENGTH: 30 base pairs
        (B) TYPE: nucleic acid
        (C) STRANDEDNESS: single
        (D) TOPOLOGY: linear

```
        (ii) MOLECULE TYPE: DNA (genomic)

(iii) HYPOTHETICAL: NO (xi) SEQUENCE DESCRIPTION: SEQ ID NO: 52:

TCTACTACTA CTGAATCAGC TGTACCAAAT                                              30

(2) INFORMATION FOR SEQ ID NO: 53:

(i) SEQUENCE CHARACTERISTICS:
            (A) LENGTH: 23 base pairs
            (B) TYPE: nucleic acid
            (C) STRANDEDNESS: unknown
            (D) TOPOLOGY: unknown (ii) MOLECULE TYPE: DNA (genomic)

(iii) HYPOTHETICAL: NO (xi) SEQUENCE DESCRIPTION: SEQ ID NO: 53:

TTTGTTACTG TGGTAGATAC CAC                                                     23

(2) INFORMATION FOR SEQ ID NO: 54:

(i) SEQUENCE CHARACTERISTICS:
            (A) LENGTH: 20 base pairs
            (B) TYPE: nucleic acid
            (C) STRANDEDNESS: unknown
            (D) TOPOLOGY: unknown (ii) MOLECULE TYPE: DNA (genomic)

(iii) HYPOTHETICAL: NO (xi) SEQUENCE DESCRIPTION: SEQ ID NO: 54:

TTTGTTACTG TGGTAGATAC                                                         20

(2) INFORMATION FOR SEQ ID NO: 55:

(i) SEQUENCE CHARACTERISTICS:
            (A) LENGTH: 23 base pairs
            (B) TYPE: nucleic acid
            (C) STRANDEDNESS: unknown
            (D) TOPOLOGY: unknown (ii) MOLECULE TYPE: DNA (genomic)

(iii) HYPOTHETICAL: NO (xi) SEQUENCE DESCRIPTION: SEQ ID NO: 55:

TTTGTTACTG TGGTAGATAC TAC                                                     23

(2) INFORMATION FOR SEQ ID NO: 56:

(i) SEQUENCE CHARACTERISTICS:
            (A) LENGTH: 20 base pairs
            (B) TYPE: nucleic acid
            (C) STRANDEDNESS: unknown
            (D) TOPOLOGY: unknown (ii) MOLECULE TYPE: DNA (genomic)

(iii) HYPOTHETICAL: NO (xi) SEQUENCE DESCRIPTION: SEQ ID NO: 56:

ACTAAATGTC AAATAAAAAG                                                         20

(2) INFORMATION FOR SEQ ID NO: 57:
```

```
    (i) SEQUENCE CHARACTERISTICS:
        (A) LENGTH: 25 base pairs
        (B) TYPE: nucleic acid
        (C) STRANDEDNESS: unknown
        (D) TOPOLOGY: unknown (ii) MOLECULE TYPE: DNA (genomic)

(iii) HYPOTHETICAL: NO (xi) SEQUENCE DESCRIPTION: SEQ ID NO: 57:

CTTATACTAA ATGTCAAATA AAAAG                                            25
```